United States Patent
Gallagher et al.

(10) Patent No.: US 8,404,824 B2
(45) Date of Patent: Mar. 26, 2013

(54) SPLICE VARIANTS OF HUMAN IL-23 RECEPTOR (IL-23R) MRNA AND USE OF A Δ9 ISOFORM IN PREDICTING INFLAMMATORY BOWEL DISEASES

(75) Inventors: Gant Gallagher, Milltown, NJ (US);
Raymond Yu, East Brunswick, NJ (US);
Shih-hsin Kan, Ewing, PA (US);
Giacomo Mancini, Millstone, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 13/438,456

(22) Filed: Apr. 3, 2012

(65) Prior Publication Data

US 2012/0245325 A1    Sep. 27, 2012

Related U.S. Application Data

(62) Division of application No. 12/386,146, filed on Apr. 14, 2009, now Pat. No. 8,206,925.

(60) Provisional application No. 61/124,092, filed on Apr. 14, 2008, provisional application No. 61/124,099, filed on Apr. 14, 2008, provisional application No. 61/124,367, filed on Apr. 14, 2008, provisional application No. 61/124,355, filed on Apr. 16, 2008.

(51) Int. Cl.
*C07H 21/02* (2006.01)
*C12P 19/34* (2006.01)

(52) U.S. Cl. ..................... 536/23.1; 435/91.1
(58) Field of Classification Search ............... None
See application file for complete search history.

(56) References Cited

U.S. PATENT DOCUMENTS 9,972,708    3/2003  Cosman et al.

OTHER PUBLICATIONS

Zhang et al. Immunogenetics 2006 vol. 57 pp. 934-943, pub online Dec. 22, 2005.*

* cited by examiner

*Primary Examiner* — Katherine Salmon
(74) *Attorney, Agent, or Firm* — Siu K. Lo

(57) ABSTRACT

There is disclosed the cloning and identification of human IL-23R splice variants caused by alternative splicing of the IL-23R mRNA in human. Alternative mRNA forms occur through skipping one, multiple full exons or partial exons, within the IL-23R gene. A total of twenty-five (25) different IL-23R transcripts were identified. A novel exon deletion (exon 9) isoform in the interleukin 23 receptor is disclosed, denoted as Δ9. The present application also describes a quantitative assay to measure different IL-23R isoform. Detection of Δ9 isoform of IL-23R is predominantly present in colon and cervical tissues. A decrease in Δ9 is observed in inflamed colon tissues in Crohn's patients. There is disclosed a method of predicting Crohn's disease by measuring Δ9 isoform of IL-23R.

1 Claim, 22 Drawing Sheets

| Isoform | Name | Target of NMD Pathway | Genbank Entry Number |
|---|---|---|---|
| Isoform-6 | Δ9 | ? (65) | AM 990318 |
| Isoform-7 | Δ5,6 | Y (72) | AM 990319 |
| Isoform-8 | Δ6,7 | N | AM 990320 |
| Isoform-9 | Δ8,9 | ? (65) | AM 990321 |
| Isoform-10 | Δ5,6,7 | ? (66) | AM 990322 |
| Isoform-11 | pΔ5 Snt | Y (106) | AM 990323 |

| | Predicted IL-23Rα protein expression | Predicted amino acids | Predicted Biological Function |
|---|---|---|---|
| WT | ATG ... TAG | 629 | Wild type IL-23Rα |
| Δ4 | ATG STOP | 123 | Short peptide, NMD candidate |
| Δ5, Δ5,8, Δ5,9 | ATG STOP | 174 | Short peptide, NMD candidate |
| Δ6 | ATG STOP | 218 | Short peptide, NMD candidate |
| Δ7 | ATG STOP | 283 | Soluble form |
| Δ8 | ATG STOP | 599 | Varied extracellular domain |
| Δ9 | ATG STOP | 356 | Soluble form |
| Δ5,6, Δ5,6,8, Δ5,6,9 | ATG STOP | 192 | Short peptide, NMD candidate |
| Δ6,7 | ATG STOP | 528 | Varied extracellular domain |
| Δ8,9 | ATG STOP | 326 | Soluble form |
| Δ5,6,7 | ATG STOP | 174 | Short peptide, NMD candidate |
| pΔ5 5 nt, pΔ5, 5nt; Δ6,7; pΔ5, 5nt; Δ8 | ATG STOP | 178 | Short peptide, NMD candidate |
| pΔ5 71 nt; pΔ5,71nt;Δ8,9 | ATG STOP | 191 | Short peptide, but no NMD |
| pΔ11 67 nt | ATG STOP | 414 | Non-responsive receptor isoform |
| pΔ5,6,7 | ATG STOP | 184 | Short peptide, NMD candidate |
| pΔ7,8; pΔ11 67 nt | ATG STOP | 293 | Soluble form |
| pΔ5,6,7; Δ9; pΔ11 67nt | ATG STOP | 260 | Soluble form |
| Δ8; pΔ11 67 nt | ATG STOP | 384 | Varied extracellular domain Non-responsive receptor isoform |

Figure 11
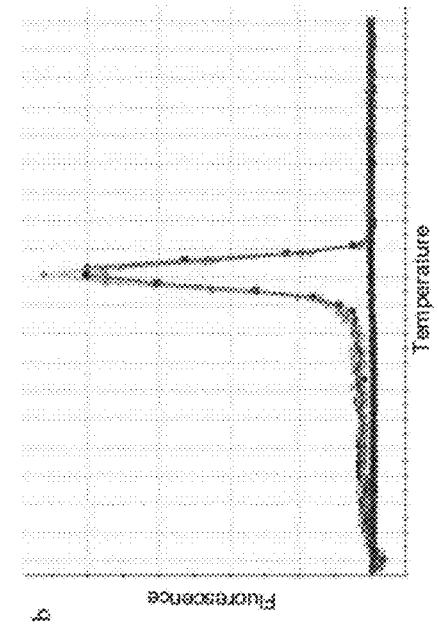
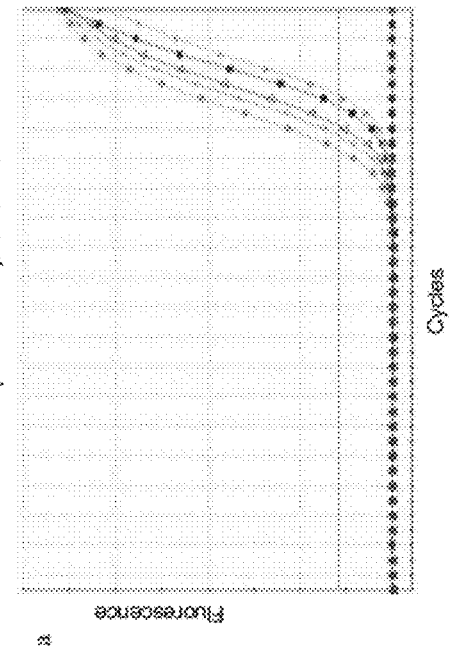
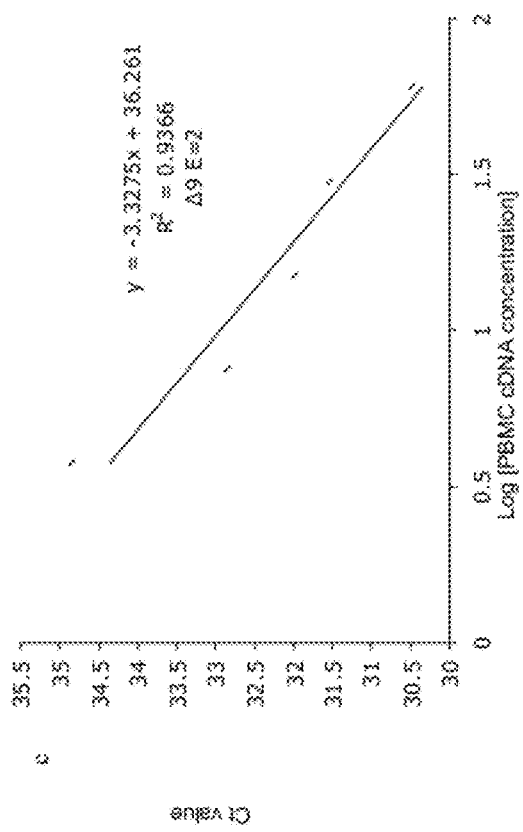

Figure 17

Summary of relative level of Δ9 in colon non-inflamed and inflamed areas

| Patient Number | Inflammatory Diseases | Area | Relative level of Δ9 |
|---|---|---|---|
| 1 | Active Crohn's | Colon non-inflamed | - |
| 1 | Active Crohn's | Colon inflamed | → |
| 2 | Active Crohn's | Colon inflamed | → |
| 3 | Active Crohn's | Colon inflamed | → |
| 4 | Active Crohn's | Colon non-inflamed scarred | - |

Figure 19

Summary of relative level of Δ9 in PBMC isolated from Healthy Individual and Active Crohn's Patient

| Donor | Inflammatory Disease | Area | Relative level of Δ9 |
|---|---|---|---|
| Healthy Individual | - | PBMC | - |
| Patient 6 | Active Crohn's | PBMC | ↓ |

SEQUENCE LISTING

<160> NUMBER OF SEQ ID NOS: 50

<210> SEQ ID NO 1
<211> LENGTH: 1110
<212> TYPE: DNA
<213> ORGANISM: Homo sapiens

<400> SEQUENCE: 1

```
gtagaaccag ccacaatttt taagatgggt atgaatatct ctatatattg ccaagcagca      60
attaagaact gccaaccaag gaaacttcat ttttataaaa atggcatcaa agaaagattt     120
caaatcacaa ggattaataa aacaacagct cggctttggt ataaaaactt tctggaacca     180
catgcttcta tgtactgcac tgctgaatgt cccaaacatt ttcaagagac actgatatgt     240
ggaaaagaca tttcttctgg atttttagaga cagaagaaga gcaacagtat ctcacctcaa     300
gctatattaa catctccact gattcattac aaggtggcaa gaagtacttg gtttgggtcc     360
aagcagcaaa cgcactaggc atggaagagt caaaacaact gcaaattcac ctggatgata     420
tagtgatacc ttctgcagcc gtcatttcca gggctgagac tataaatgct acagtgccca     480
agaccataat ttattgggat agtcaaacaa caattgaaaa ggtttcctgt gaaatgagat     540
acaaggctac aacaaaccaa acttggaatg ttaaagaatt tgacaccaat tttacatatg     600
tgcaacagtc agaattctac ttggagccaa acattaagta cgtatttcaa gtgagatgtc     660
aagaaacagg caaaggtac tggcagcctt ggagttcacc gttttttcat aaaacacctg     720
aaacagttcc ccaggtcaca tcaaaagcat tccaacatga cacatggaat tctgggctaa     780
cagttgcttc catctctaca gggcacctta cttctgacaa cagaggagac attggacttt     840
tattgggaat gatcgtcttt gctgttatgt tgtcaattct ttctttgatt gggatattta     900
acagatcatt ccgaactggg attaaaagaa ggatcttatt gttaatacca aagtggcttt     960
atgaagatat tcctaatatg aaaaacagca atgttgtgaa aatgctacag gaaaatagtg    1020
aacttatgaa taataattcc agtgagcagg tcctatatgt tgatcccatg attacagaga    1080
taaagaaat cttcatccca gaacacaagc                                      1110
```

<210> SEQ ID NO 2
<211> LENGTH: 740
<212> TYPE: DNA
<213> ORGANISM: Homo sapiens

<400> SEQUENCE: 2

```
aatgctggga agctcaccta catagacaca aaatacgtgg tacatgtgaa gagtgatacc      60
ttctgcagcc gtcatttcca gggctgagac tataaatgct acagtgccca agaccataat     120
ttattgggat agtcaaacaa caattgaaaa ggtttcctgt gaaatgagat acaaggctac     180
aacaaaccaa acttggaatg ttaaagaatt tgacaccaat tttacatatg tgcaacagtc     240
agaattctac ttggagccaa acattaagta cgtatttcaa gtgagatgtc aagaaacagg     300
caaaggtac tggcagcctt ggagttcacc gttttttcat aaaacacctg aaacagttcc     360
ccaggtcaca tcaaaagcat tccaacatga cacatggaat tctgggctaa cagttgcttc     420
catctctaca gggcacctta cttctgacaa cagaggagac attggacttt tattgggaat     480
gatcgtcttt gctgttatgt tgtcaattct ttctttgatt gggatattta acagatcatt     540
ccgaactggg attaaaagaa ggatcttatt gttaatacca aagtggcttt atgaagatat     600
tcctaatatg aaaaacagca atgttgtgaa aatgctacag gaaaatagtg aacttatgaa     660
```

```
taataattcc agtgagcagg tcctatatgt tgatcccatg attacagaga taaagaaat    720 cttcatccca gaacacaagc                                               740

<210> SEQ ID NO 3
<211> LENGTH: 755
<212> TYPE: DNA
<213> ORGANISM: Homo sapiens

<400> SEQUENCE: 3
aatgctggga agctcaccta catagacaca aaatacgtgg tacatgtgaa gagtttagag     60
acagaagaag agcaacagta tctcacctca agctatatta acatctccac tgattcatta   120
caaggtggca agaagtactt ggtttgggtc caagcagcaa acgcactagg catggaagag   180
tcaaaacaac tgcaaattca cctggatgat ataggtaaaa gaatttgaca ccaattttac   240
atatgtgcaa cagtcagaat tctacttgga gccaaacatt aagtacgtat ttcaagtgag   300
atgtcaagaa acaggcaaaa ggtactggca gccttggagt tcaccgtttt ttcataaaac   360
acctgaaaca gttccccagg tcacatcaaa agcattccaa catgacacat ggaattctgg   420
gctaacagtt gcttccatct ctacagggca ccttacttct gacaacagag agacattgg    480 acttttattg ggaatgatcg tctttgctgt tatgttgtca attctttctt tgattgggat   540
atttaacaga tcattccgaa ctgggattaa aagaaggatc ttattgttaa taccaaagtg   600
gctttatgaa gatattccta atatgaaaaa cagcaatgtt gtgaaaatgc tacaggaaaa   660
tagtgaactt atgaataata attccagtga gcaggtccta tatgttgatc ccatgattac   720
agagataaaa gaaatcttca tcccagaaca caagc                              755

<210> SEQ ID NO 4
<211> LENGTH: 744
<212> TYPE: DNA
<213> ORGANISM: Homo sapiens

<400> SEQUENCE: 4
aatgctggga agctcaccta catagacaca aaatacgtgg tacatgtgaa gagtttagag     60
acagaagaag agcaacagta tctcacctca agctatatta acatctccac tgattcatta   120
caaggtggca agaagtactt ggtttgggtc caagcagcaa acgcactagg catggaagag   180
tcaaaacaac tgcaaattca cctggatgat atagtgatac cttctgcagc cgtcatttcc   240
agggctgaga ctataaatgc tacagtgccc aagaccataa tttattggga tagtcaaaca   300
acaattgaaa ggtttcctg tgaaatgaga tacaaggcta caacaaacca aacttggaat   360
ttccccaggt cacatcaaaa gcattccaac atgacacatg gaattctggg ctaacagttg   420
cttccatctc tacagggcac cttacttctg acaacagagg agacattgga ctttttattgg   480 gaatgatcgt ctttgctgtt atgttgtcaa ttctttcttt gattgggata tttaacagat   540
cattccgaac tgggattaaa agaaggatct tattgttaat accaaagtgg ctttatgaag   600
atattcctaa tatgaaaaac agcaatgttg tgaaaatgct acaggaaaat agtgaactta   660
tgaataataa ttccagtgag caggtcctat atgttgatcc catgattaca gagataaaag   720
aaatcttcat cccagaacac aagc                                          744

<210> SEQ ID NO 5
<211> LENGTH: 811
<212> TYPE: DNA
<213> ORGANISM: Homo sapiens

<400> SEQUENCE: 5
```

```
aatgctggga agctcaccta catagacaca aaatacgtgg tacatgtgaa gagtttagag      60
acagaagaag agcaacagta tctcacctca agctatatta acatctccac tgattcatta     120
caaggtggca agaagtactt ggtttgggtc caagcagcaa acgcactagg catggaagag     180
tcaaaacaac tgcaaattca cctgatgat atagtgatac cttctgcagc cgtcatttcc      240
agggctgaga ctataaatgc tacagtgccc aagaccataa tttattggga tagtcaaaca     300
acaattgaaa aggtttcctg tgaaatgaga tacaaggcta caacaaacca aacttggaat    360
gttaaagaat ttgacaccaa ttttacatat gtgcaacagt cagaattcta cttggagcca    420
aacattaagt acgtatttca agtgagatgt caagaaacag gcaaaaggta ctggcagcct    480
tggagttcac cgttttttca taaaacacct gaaacagaca acagaggaga cattggactt    540
ttattgggaa tgatcgtctt tgctgttatg ttgtcaattc tttctttgat tgggatattt    600
aacagatcat tccgaactgg gattaaaaga aggatcttat tgttaatacc aaagtggctt    660
tatgaagata ttcctaatat gaaaaacagc aatgttgtga aaatgctaca ggaaaatagt    720
gaacttatga ataataattc cagtgagcag gtcctatatg ttgatcccat gattacagag    780
ataaaagaaa tcttcatccc agaacacaag c                                    811

<210> SEQ ID NO 6
<211> LENGTH: 798
<212> TYPE: DNA
<213> ORGANISM: Homo sapiens

<400> SEQUENCE: 6
aatgctggga agctcaccta catagacaca aaatacgtgg tacatgtgaa gagtttagag      60
acagaagaag agcaacagta tctcacctca agctatatta acatctccac tgattcatta     120
caaggtggca agaagtactt ggtttgggtc caagcagcaa acgcactagg catggaagag     180
tcaaaacaac tgcaaattca cctgatgat atagtgatac cttctgcagc cgtcatttcc      240
agggctgaga ctataaatgc tacagtgccc aagaccataa tttattggga tagtcaaaca     300
acaattgaaa aggtttcctg tgaaatgaga tacaaggcta caacaaacca aacttggaat    360
gttaaagaat ttgacaccaa ttttacatat gtgcaacagt cagaattcta cttggagcca    420
aacattaagt acgtatttca agtgagatgt caagaaacag gcaaaaggta ctggcagcct    480
tggagttcac cgttttttca taaaacacct gaaacagttc cccaggtcac atcaaaagca    540
ttccaacatg acacatggaa ttctgggcta acagttgctt ccatctctac agggcacctt    600
acttctggat aaaagaagg atcttattgt taataccaaa gtggctttat gaagatattc     660
ctaatatgaa aaacagcaat gttgtgaaaa tgctacagga aaatagtgaa cttatgaata    720
ataattccag tgagcaggtc ctatatgttg atcccatgat tacagagata aagaaatct    780 tcatcccaga acacaagc                                                    798

<210> SEQ ID NO 7
<211> LENGTH: 594
<212> TYPE: DNA
<213> ORGANISM: Homo sapiens

<400> SEQUENCE: 7
aatgctggga agctcaccta catagacaca aaatacgtgg tacatgtgaa gaggttaaag      60
aatttgacac caatttttaca tatgtgcaac agtcagaatt ctacttggag ccaaacatta    120
agtacgtatt tcaagtgaga tgtcaagaaa caggcaaaag gtactggcag ccttggagtt    180
caccgttttt tcataaaaca cctgaaacag ttccccaggt cacatcaaaa gcattccaac    240
```

```
atgacacatg gaattctggg ctaacagttg cttccatctc tacagggcac cttacttctg    300
acaacagaga agacattgga cttttattgg gaatgatcgt ctttgctgtt atgttgtcaa    360
ttctttcttt gattgggata tttaacagat cattccgaac tgggattaaa agaaggatct    420
tattgttaat accaaagtgg ctttatgaag atattcctaa tatgaaaaac agcaatgttg    480
tgaaaatgct acaggaaaat agtgaactta tgaataataa ttccagtgag caggtcctat    540
atgttgatcc catgattaca gagataaaag aaatcttcat cccagaacac aagc          594

<210> SEQ ID NO 8
<211> LENGTH: 598
<212> TYPE: DNA
<213> ORGANISM: Homo sapiens

<400> SEQUENCE: 8
aatgctggga agctcaccta catagacaca aaatacgtgg tacatgtgaa gagtttagag     60
acagaagaag agcaacagta tctcacctca agctatatta acatctccac tgattcatta    120
caaggtggca agaagtactt ggtttgggtc caagcagcaa acgcactagg catggaagag    180
tcaaaacaac tgcaaattca cctggatgat atagttcccc aggtcacatc aaaagcattc    240
caacatgaca catggaattc tgggctaaca gttgcttcca tctctacagg gcaccttact    300
tctgacaaca gaggagacat tggactttta ttgggaatga tcgtctttgc tgttatgttg    360
tcaattcttt ctttgattgg gatatttaac agatcattcc gaactgggat aaaagaagg    420 atcttattgt taataccaaa gtggctttat gaagatattc ctaatatgaa aaacagcaat    480
gttgtgaaaa tgctacagga aaatagtgaa cttatgaata taattccag tgagcaggtc    540 ctatatgttg atcccatgat tacagagata aagaaatct tcatcccaga acacaagc      598

<210> SEQ ID NO 9
<211> LENGTH: 708
<212> TYPE: DNA
<213> ORGANISM: Homo sapiens

<400> SEQUENCE: 9
aatgctggga agctcaccta catagacaca aaatacgtgg tacatgtgaa gagtttagag     60
acagaagaag agcaacagta tctcacctca agctatatta acatctccac tgattcatta    120
caaggtggca agaagtactt ggtttgggtc caagcagcaa acgcactagg catggaagag    180
tcaaaacaac tgcaaattca cctggatgat atagtgatac cttctgcagc cgtcatttcc    240
agggctgaga ctaaaatgc tacagtgccc aagaccataa tttattggga tagtcaaaca    300
acaattgaaa aggtttcctg tgaaatgaga tacaaggcta caacaaacca aacttggaat    360
gttaaagaat ttgacaccaa ttttacatat gtgcaacagt cagaattcta cttggagcca    420
aacattaagt acgtatttca agtgagatgt caagaaacag gcaaaggta ctggcagcct    480 tggagttcac cgtttttca taaaacacct gaaacaggat taaagaagg atcttattgt    540 taataccaaa gtggctttat gaagatattc ctaatatgaa aaacagcaat gttgtgaaaa    600
tgctacagga aaatagtgaa cttatgaata taattccag tgagcaggtc ctatatgttg    660
atcccatgat tacagagata aagaaatct tcatcccaga acacaagc                 708

<210> SEQ ID NO 10
<211> LENGTH: 437
<212> TYPE: DNA
<213> ORGANISM: Homo sapiens

<400> SEQUENCE: 10
```

| aatgctggga agctcaccta catagacaca aaatacgtgg tacatgtgaa gagttcccca | 60 |
| ggtcacatca aaagcattcc aacatgcaca atggaattct gggctaacag ttgcttccat | 120 |
| ctctacaggg caccttactt ctgacaacag aggagacatt ggactttat tgggaatgat | 180 |
| cgtctttgct gttatgttgt caattctttc tttgattggg atatttaaca gatcattccg | 240 |
| aactgggatt aaaagaagga tcttattgtt aataccaaag tggctttatg aagatattcc | 300 |
| taatatgaaa acagcaatg ttgtgaaaat gctacaggaa aatagtgaac ttatgaataa | 360 |
| taattccagt gagcaggtcc tatatgttga tcccatgatt acagagataa agaaatctt | 420 |
| catcccagaa cacaagc | 437 |

<210> SEQ ID NO 11
<211> LENGTH: 896
<212> TYPE: DNA
<213> ORGANISM: Homo sapiens

<400> SEQUENCE: 11

| aatgctggga agctcaccta catagacaca aaatacgtgg tacatgtgaa gagagacaga | 60 |
| agaagagcaa cagtatctca cctcaagcta tattaacatc tccactgatt cattacaagg | 120 |
| tggcaagaag tacttggttt gggtccaagc agcaaacgca ctaggcatgg aagagtcaaa | 180 |
| acaactgcaa attcacctgg atgatatagt gataccttct gcagccgtca tttccagggc | 240 |
| tgagactata aatgctacag tgcccaagac cataatttat tgggatagtc aaacaacaat | 300 |
| tgaaaaggtt tcctgtgaaa tgagatacaa ggctacaaca aaccaaactt ggaatgttaa | 360 |
| agaatttgac accaatttta catatgtgca acagtcagaa ttctacttgg agccaaacat | 420 |
| taagtacgta tttcaagtga gatgtcaaga acaggcaaa aggtactggc agccttggag | 480 |
| ttcaccgttt tttcataaaa cacctgaaac agttccccag gtcacatcaa aagcattcca | 540 |
| acatgacaca tggaattctg gctaacagt tgcttccatc tctacagggc accttacttc | 600 |
| tgacaacaga ggagacattg actttttatt gggaatgatc gtctttgctg ttatgttgtc | 660 |
| aattctttct tgattgggta tatttaacag atcattccga actgggatta aagaaggat | 720 |
| cttattgtta ataccaaagt ggctttatga agatattcct aatatgaaaa acagcaatgt | 780 |
| tgtgaaaatg ctacaggaaa atagtgaact tatgaataat aattccagtg agcaggtcct | 840 |
| atatgttgat cccatgatta cagagataaa gaaatcttc atcccagaac acaagc | 896 |

<210> SEQ ID NO 12
<211> LENGTH: 830
<212> TYPE: DNA
<213> ORGANISM: Homo sapiens

<400> SEQUENCE: 12

| aatgctggga agctcaccta catagacaca aaatacgtgg tacatgtgaa gaggtggcaa | 60 |
| gaagtacttg gtttgggtcc aagcagcaaa cgcactaggc atggaagagt caaaacaact | 120 |
| gcaaattcac ctggatgata tagtgatacc ttctgcagcc gtcatttcca gggctgagac | 180 |
| tataaatgct acagtgccca agaccataat ttattgggat agtcaaacaa caattgaaaa | 240 |
| ggtttcctgt gaaatgagat acaaggctac aacaaaccaa acttggaatg ttaaagaatt | 300 |
| tgacaccaat tttacatatg tgcaacagtc agaattctac ttggagccaa acattaagta | 360 |
| cgtatttcaa gtgagatgtc aagaaacagg caaaaggtac tggcagcctt ggagttcacc | 420 |
| gttttttcat aaaacacctg aaacagttcc ccaggtcaca tcaaaagcat tccaacatga | 480 |
| cacatggaat tctgggctaa cagttgcttc catctctaca gggcacctta cttctgacaa | 540 |

| | |
|---|---:|
| cagaggagac attggacttt tattgggaat gatcgtcttt gctgttatgt tgtcaattct | 600 |
| ttctttgatt gggatattta acagatcatt ccgaactggg attaaagaaa ggatcttatt | 660 |
| gttaatacca aagtggcttt atgaagatat tcctaatatg aaaaacagca atgttgtgaa | 720 |
| aatgctacag gaaaatagtg aacttatgaa taataattcc agtgagcagg tcctatatgt | 780 |
| tgatcccatg attacagaga taaagaaat cttcatccca gaacacaagc | 830 |

<210> SEQ ID NO 13
<211> LENGTH: 834
<212> TYPE: DNA
<213> ORGANISM: Homo sapiens

<400> SEQUENCE: 13

| | |
|---|---:|
| aatgctggga agctcaccta catagacaca aaatacgtgg tacatgtgaa gagtttagag | 60 |
| acagaagaag agcaacagta tctcacctca agctatatta acatctccac tgattcatta | 120 |
| caaggtggca agaagtactt ggtttgggtc caagcagcaa acgcactagg catggaagag | 180 |
| tcaaaacaac tgcaaattca cctggatgat atagtgatac cttctgcagc cgtcatttcc | 240 |
| agggctgaga ctataaatgc tacagtgccc aagaccataa tttattggga tagtcaaaca | 300 |
| acaattgaaa aggtttcctg tgaaatgaga tacaaggcta caacaaacca aacttggaat | 360 |
| gttaaagaat ttgacaccaa ttttacatat gtgcaacagt cagaattcta cttggagcca | 420 |
| aacattaagt acgtatttca agtgagatgt caagaaacag gcaaaggta ctggcagcct | 480 |
| tggagttcac cgttttttca taaaacacct gaaacagttc cccaggtcac atcaaaagca | 540 |
| ttccaacatg acacatggaa ttctgggcta acagttgctt ccatctctac agggcacctt | 600 |
| acttctgaca acagaggaga cattggactt ttattgggaa tgatcgtctt tgctgttatg | 660 |
| ttgtcaattc tttctttgat tgggatattt aacagatcat tccgaactgg gattaaaaga | 720 |
| aggatcttat tgttaatacc aaagtggctt tatgaagata ttcctaatat gaaaaacagc | 780 |
| aatgttgtga aatgctaca gagataaaag aaatcttcat cccagaacac aagc | 834 |

<210> SEQ ID NO 14
<211> LENGTH: 518
<212> TYPE: DNA
<213> ORGANISM: Homo sapiens

<400> SEQUENCE: 14

| | |
|---|---:|
| aatgctggga agctcaccta catagacaca aaatacgtgg tacatgtgaa gagtttagag | 60 |
| acagaagaag agcaacagta tctcacctca agctatatta acatctccac tgattcataa | 120 |
| aacacctgaa acagttcccc aggtcacatc aaaagcattc caacatgaca catggaattc | 180 |
| tgggctaaca gttgcttcca tctctacagg gcaccttact tctgacaaca gaggagacat | 240 |
| tggactttta ttgggaatga tcgtctttgc tgttatgttg tcaattcttt ctttgattgg | 300 |
| gatatttaac agatcattcc gaactgggat taaagaagg atcttattgt taataccaaa | 360 |
| gtggctttat gaagatattc ctaatatgaa aaacagcaat gttgtgaaaa tgctacagga | 420 |
| aaatagtgaa cttatgaata ataattccag tgagcaggtc ctatatgttg atcccatgat | 480 |
| tacagagata aagaaatct tcatcccaga acacaagc | 518 |

<210> SEQ ID NO 15
<211> LENGTH: 650
<212> TYPE: DNA
<213> ORGANISM: Homo sapiens

<400> SEQUENCE: 15

-continued

```
aatgctggga agctcaccta catagacaca aaatacgtgg tacatgtgaa gagtgatacc    60
ttctgcagcc gtcatttcca gggctgagac tataaatgct acagtgccca agaccataat   120
ttattgggat agtcaaacaa caattgaaaa ggtttcctgt gaaatgagat acaaggctac   180
aacaaaccaa acttggaatg ttaaagaatt tgacaccaat tttacatatg tgcaacagtc   240
agaattctac ttggagccaa acattaagta cgtatttcaa gtgagatgtc aagaaacagg   300
caaaaggtac tggcagcctt ggagttcacc gttttttcat aaaacacctg aaacagacaa   360
cagaggagac attggacttt tattgggaat gatcgtcttt gctgttatgt tgtcaattct   420
ttctttgatt gggatattta acagatcatt ccgaactggg attaaaagaa ggatcttatt   480
gttaatacca aagtggcttt atgaagatat tcctaatatg aaaaacagca atgttgtgaa   540
aatgctacag gaaaatagtg aacttatgaa taataattcc agtgagcagg tcctatatgt   600
tgatcccatg attacagaga taaagaaat cttcatccca gaacacaagc              650
```

<210> SEQ ID NO 16
<211> LENGTH: 637
<212> TYPE: DNA
<213> ORGANISM: Homo sapiens

<400> SEQUENCE: 16

```
aatgctggga agctcaccta catagacaca aaatacgtgg tacatgtgaa gagtgatacc    60
ttctgcagcc gtcatttcca gggctgagac tataaatgct acagtgccca agaccataat   120
ttattgggat agtcaaacaa caattgaaaa ggtttcctgt gaaatgagat acaaggctac   180
aacaaaccaa acttggaatg ttaaagaatt tgacaccaat tttacatatg tgcaacagtc   240
agaattctac ttggagccaa acattaagta cgtatttcaa gtgagatgtc aagaaacagg   300
caaaaggtac tggcagcctt ggagttcacc gttttttcat aaaacacctg aaacagttcc   360
ccaggtcaca tcaaaagcat tccaacatga cacatggaat tctgggctaa cagttgcttc   420
catctctaca gggcacctta cttctggatt aaaagaagga tcttattgtt aataccaaag   480
tggctttatg aagatattcc taatatgaaa aacagcaatg ttgtgaaaat gctacaggaa   540
aatagtgaac ttatgaataa taattccagt gagcaggtcc tatatgttga tcccatgatt   600
acagagataa agaaatctt catcccagaa cacaagc                            637
```

<210> SEQ ID NO 17
<211> LENGTH: 504
<212> TYPE: DNA
<213> ORGANISM: Homo sapiens

<400> SEQUENCE: 17

```
aatgctggga agctcaccta catagacaca aaatacgtgg tacatgtgaa gaggttaaag    60
aatttgacac caattttaca tatgtgcaac agtcagaatt ctacttggag ccaaacatta   120
agtacgtatt tcaagtgaga tgtcaagaaa caggcaaaag gtactggcag ccttggagtt   180
caccgttttt tcataaaaca cctgaaacag acaacagagg agacattgga ctttttattgg   240
gaatgatcgt ctttgctgtt atgttgtcaa ttctttcttt gattgggata tttaacagat   300
cattccgaac tgggattaaa agaaggatct tattgttaat accaaagtgg ctttatgaag   360
atattcctaa tatgaaaaac agcaatgttg tgaaaatgct acaggaaaat agtgaactta   420
tgaataataa ttccagtgag caggtcctat atgttgatcc catgattaca gagataaaag   480
aaatcttcat cccagaacac aagc                                         504
```

<210> SEQ ID NO 18

```
<211> LENGTH: 491
<212> TYPE: DNA
<213> ORGANISM: Homo sapiens

<400> SEQUENCE: 18
aatgctggga agctcaccta catagacaca aaatacgtgg tacatgtgaa gaggttaaag      60
aatttgacac caattttaca tatgtgcaac agtcagaatt ctacttggag ccaaacatta     120
agtacgtatt tcaagtgaga tgtcaagaaa caggcaaaag gtactggcag ccttggagtt     180
caccgttttt tcataaaaca cctgaaacag ttccccaggt cacatcaaaa gcattccaac     240 atgcacatg gaattctggg ctaacagttg cttccatctc tacagggcac cttacttctg      300
gattaaaaga aggatcttat tgttaatacc aaagtggctt tatgaagata ttcctaatat     360
gaaaaacagc aatgttgtga aatgctaca ggaaaatagt gaacttatga ataataattc      420
cagtgagcag gtcctatatg ttgatcccat gattacagag ataaaagaaa tcttcatccc     480
agaacacaag c                                                          491

<210> SEQ ID NO 19
<211> LENGTH: 670
<212> TYPE: DNA
<213> ORGANISM: Homo sapiens

<400> SEQUENCE: 19
aatgctggga agctcaccta catagacaca aaatacgtgg tacatgtgaa gagtttagag      60
acagaagaag agcaacagta tctcacctca agctatatta acatctccac tgattcatta    120
caaggtggca agaagtactt ggtttgggtc caagcagcaa acgcactagg catggaagag    180 tcaaacaac tgcaaattca cctggatgat atagtgatac cttctgcagc cgtcatttcc     240
agggctgaga ctataaatgc tacagtgccc aagaccataa tttattggga tagtcaaaca    300
acaattgaaa aggtttcctg tgaaatgaga tacaaggcta caacaaacca aacttggaat    360
gttaaagaat ttgacaccaa ttttacatat gtgcaacagt cagaattcta cttggagcca    420
aacattaagg caccttactt ctgacaacag aggagacatt ggactttat tgggaatgat     480 cgtctttgct gttatgttgt caattctttc tttgattggg atatttaaca gatcattccg    540
aactgggatt aaaagaagga tcttattgtt aataccaaag tggctttatg aagatattcc    600
taatatgaaa aacagcaatg ttgtgaaaat gctacagaga taaagaaat cttcatccca     660 gaacacaagc                                                           670

<210> SEQ ID NO 20
<211> LENGTH: 437
<212> TYPE: DNA
<213> ORGANISM: Homo sapiens

<400> SEQUENCE: 20
aatgctggga agctcaccta catagacaca aaatacgtgg tacatgtgaa gagtttagag      60
acagaagaag agcaacagta tctcacctca agctatatta acatctccac tgattcatta    120
caaggtggca agaagtacgt atttcaagtg agatgtcaag aaacaggcaa aaggtactgg    180
cagccttgga gttcaccgtt ttttcataaa acacctgaaa cagttcccca ggtcacatca    240
aaagcattcc aacatgacac atggaattct gggctaacag ttgcttccat ctctacaggg    300
caccttactt ctggattaaa agaaggatct tattgttaat accaaagtgg ctttatgaag    360
atattcctaa tatgaaaaac agcaatgttg tgaaaatgct acagagataa agaaatctt     420 catcccagaa cacaagc                                                   437
```

<210> SEQ ID NO 21
<211> LENGTH: 593
<212> TYPE: DNA
<213> ORGANISM: Homo sapiens

<400> SEQUENCE: 21

| | |
|---|---|
| aatgctggga agctcaccta catagacaca aaatacgtgg tacatgtgaa gagagacaga | 60 |
| agaagagcaa cagtatctca cctcaagcta tattaacatc tccactgatt cattacaagg | 120 |
| tggcaagaag tacttggttt gggtccaagc agcaaacgca ctaggcatgg aagagtcaaa | 180 |
| acaactgcaa attcacctgg atgatatagt tccccaggtc acatcaaaag cattccaaca | 240 |
| tgacacatgg aattctgggc taacagttgc ttccatctct acagggcacc ttacttctga | 300 |
| caacagagga gacattggac ttttattggg aatgatcgtc tttgctgtta tgttgtcaat | 360 |
| tctttctttg attgggatat ttaacagatc attccgaact gggattaaaa gaaggatctt | 420 |
| attgttaata ccaaagtggc tttatgaaga tattcctaat atgaaaaaca gcaatgttgt | 480 |
| gaaaatgcta caggaaaata gtgaacttat gaataataat tccagtgagc aggtcctata | 540 |
| tgttgatccc atgattacag agataaaaga aatcttcatc ccagaacaca agc | 593 |

<210> SEQ ID NO 22
<211> LENGTH: 637
<212> TYPE: DNA
<213> ORGANISM: Homo sapiens

<400> SEQUENCE: 22

| | |
|---|---|
| aatgctggga agctcaccta catagacaca aaatacgtgg tacatgtgaa gaggtggcaa | 60 |
| gaagtacttg gtttgggtcc aagcagcaaa cgcactaggc atggaagagt caaaacaact | 120 |
| gcaaattcac ctggatgata tagtgatacc ttctgcagcc gtcatttcca gggctgagac | 180 |
| tataaatgct acagtgccca agaccataat ttattgggat agtcaaacaa caattgaaaa | 240 |
| ggtttcctgt gaaatgagat acaaggctac aacaaaccaa acttggaatg ttaaagaatt | 300 |
| tgacaccaat tttacatatg tgcaacagtc agaattctac ttggagccaa acattaagta | 360 |
| cgtatttcaa gtgagatgtc aagaaacagg caaaaggtac tggcagcctt ggagttcacc | 420 |
| gttttttcat aaaacacctg aacaggatt aaaagaagga tcttattgtt aataccaaag | 480 |
| tggctttatg aagatattcc taatatgaaa acagcaatg ttgtgaaaat gctacaggaa | 540 |
| aatagtgaac ttatgaataa taattccagt gagcaggtcc tatatgttga tcccatgatt | 600 |
| acagagataa agaaatctt catcccagaa cacaagc | 637 |

<210> SEQ ID NO 23
<211> LENGTH: 744
<212> TYPE: DNA
<213> ORGANISM: Homo sapiens

<400> SEQUENCE: 23

| | |
|---|---|
| aatgctggga agctcaccta catagacaca aaatacgtgg tacatgtgaa gagtttagag | 60 |
| acagaagaag agcaacagta tctcacctca agctatatta acatctccac tgattcatta | 120 |
| caaggtggca agaagtactt ggtttgggtc aagcagcaa acgcactagg catggaagag | 180 |
| tcaaaacaac tgcaaattca cctggatgat atagtgatac cttctgcagc cgtcatttcc | 240 |
| agggctgaga ctataaatgc tacagtgccc aagaccataa tttattggga tagtcaaaca | 300 |
| acaattgaaa aggtttcctg tgaaatgaga tacaaggcta acaaaacca acttggaat | 360 |
| gttaaagaat ttgacaccaa ttttacatat gtgcaacagt cagaattcta cttggagcca | 420 |

| | |
|---|---:|
| aacattaagt acgtatttca agtgagatgt caagaaacag gcaaaaggta ctggcagcct | 480 |
| tggagttcac cgttttttca taaaacacct gaaacagaca acagaggaga cattggactt | 540 |
| ttattgggaa tgatcgtctt tgctgttatg ttgtcaattc tttctttgat tgggatattt | 600 |
| aacagatcat tccgaactgg gattaaaaga aggatcttat tgttaatacc aaagtggctt | 660 |
| tatgaagata ttcctaatat gaaaaacagc aatgttgtga aaatgctaca gagataaaag | 720 |
| aaatcttcat cccagaacac aagc | 744 |

<210> SEQ ID NO 24
<211> LENGTH: 806
<212> TYPE: DNA
<213> ORGANISM: Homo sapiens

<400> SEQUENCE: 24

| | |
|---|---:|
| aatgctggga agctcaccta catagacaca aaatacgtgg tacatgtgaa gagagacaga | 60 |
| agaagagcaa cagtatctca cctcaagcta tattaacatc tccactgatt cattacaagg | 120 |
| tggcaagaag tacttggttt gggtccaagc agcaaacgca ctaggcatgg aagagtcaaa | 180 |
| acaactgcaa attcacctgg atgatatagt gataccttct gcagccgtca tttccagggc | 240 |
| tgagactata aatgctacag tgcccaagac cataatttat tgggatagtc aaacaacaat | 300 |
| tgaaaaggtt tcctgtgaaa tgagatacaa ggctacaaca aaccaaactt ggaatgttaa | 360 |
| agaatttgac accaatttta catatgtgca acagtcagaa ttctacttgg agccaaacat | 420 |
| taagtacgta tttcaagtga gatgtcaaga acaggcaaa aggtactggc agccttggag | 480 |
| ttcaccgttt tttcataaaa cacctgaaac agacaacaga ggagacattg acttttatt | 540 |
| gggaatgatc gtctttgctg ttatgttgtc aattctttct tgattggga tatttaacag | 600 |
| atcattccga actgggatta aagaaggat cttattgtta ataccaaagt ggctttatga | 660 |
| agatattcct aatatgaaaa acagcaatgt tgtgaaaatg ctacaggaaa atagtgaact | 720 |
| tatgaataat aattccagtg agcaggtcct atatgttgat cccatgatta cagagataaa | 780 |
| agaaatcttc atcccagaac acaagc | 806 |

<210> SEQ ID NO 25
<211> LENGTH: 992
<212> TYPE: DNA
<213> ORGANISM: Homo sapiens

<400> SEQUENCE: 25

| | |
|---|---:|
| aatgctggga agctcaccta catagacaca aaatacgtgg tacatgtgaa gaggtggcaa | 60 |
| gaagtacttg gtttgggtcc aagcagcaaa cgcactaggc atggaagagt caaaacaact | 120 |
| gcaaattcac ctggatgata tagtgatacc ttctgcagcc gtcatttcca gggctgagac | 180 |
| tataaatgct acagtgccca agaccataat ttattgggat agtcaaacaa caattgaaaa | 240 |
| ggtttcctgt gaaatgagat acaaggctac aacaaaccaa acttggaatg ttaaagaatt | 300 |
| tgacaccaat tttacatatg tgcaacagtc agaattctac ttggagccaa acattaagta | 360 |
| cgtatttcaa gtgagatgtc aagaaacagg caaaaggtac tggcagcctt ggagttcacc | 420 |
| gttttttcat aaaacacctg aaacagttcc ccaggtcaca tcaaaagcat tccaacatga | 480 |
| cacatggaat tctgggctaa cagttgcttc catctctaca gggcacctta cttctgacaa | 540 |
| cagaggagac attggacttt tattgggaat gatcgtcttt gctgttatgt tgtcaattct | 600 |
| ttctttgatt gggatattta acagatcatt ccgaactggg ttttggtatc agaatgatgc | 660 |
| tggcctcata aaatgagtta gggagtattc cctctttttc tactgtttgg aacagtttca | 720 |

```
gaaggaatgg taccagctcc tctttgtacc tctggtagaa tgtggctgtg aatccgtctg    780
gtcctggact ttttttgatt ggattaaaag aaggatctta ttgttaatac caaagtggct    840
ttatgaagat attcctaata tgaaaaacag caatgttgtg aaaatgctac aggaaaatag    900
tgaacttatg aataataatt ccagtgagca ggtcctatat gttgatccca tgattacaga    960
gataaaagaa atcttcatcc cagaacacaa gc                                  992
```

```
<210> SEQ ID NO 26
<211> LENGTH: 20
<212> TYPE: DNA
<213> ORGANISM: Homo sapiens

<400> SEQUENCE: 26
gtagaaccag ccacaatttt                                                 20

<210> SEQ ID NO 27
<211> LENGTH: 24
<212> TYPE: DNA
<213> ORGANISM: Homo sapiens

<400> SEQUENCE: 27
aatgctggga agctcaccta cata                                            24

<210> SEQ ID NO 28
<211> LENGTH: 25
<212> TYPE: DNA
<213> ORGANISM: Homo sapiens

<400> SEQUENCE: 28
gcttgtgttc tgggatgaag atttc                                           25

<210> SEQ ID NO 29
<211> LENGTH: 20
<212> TYPE: DNA
<213> ORGANISM: Homo sapiens

<400> SEQUENCE: 29
catgacttgc acctggaatg                                                 20

<210> SEQ ID NO 30
<211> LENGTH: 20
<212> TYPE: DNA
<213> ORGANISM: Homo sapiens

<400> SEQUENCE: 30
gcttggaccc aaaccaagta                                                 20

<210> SEQ ID NO 31
<211> LENGTH: 24
<212> TYPE: DNA
<213> ORGANISM: Homo sapiens

<400> SEQUENCE: 31
ggcaccttac ttctggatta aaag                                            24

<210> SEQ ID NO 32
<211> LENGTH: 20
<212> TYPE: DNA
<213> ORGANISM: Homo sapiens

<400> SEQUENCE: 32
ggacctgctc actggaatta                                                 20
```

```
<210> SEQ ID NO 33
<211> LENGTH: 14
<212> TYPE: DNA
<213> ORGANISM: Homo sapiens

<400> SEQUENCE: 33
tgtgaagagg tagg                                                         14

<210> SEQ ID NO 34
<211> LENGTH: 24
<212> TYPE: DNA
<213> ORGANISM: Homo sapiens

<400> SEQUENCE: 34
tttgttttaa gtttagagac agaa                                              24

<210> SEQ ID NO 35
<211> LENGTH: 17
<212> TYPE: DNA
<213> ORGANISM: Homo sapiens

<400> SEQUENCE: 35
atgctacagg taaccta                                                      17

<210> SEQ ID NO 36
<211> LENGTH: 28
<212> TYPE: DNA
<213> ORGANISM: Homo sapiens

<400> SEQUENCE: 36
gatcccatga ttacagagat aaaagaaa                                          28

<210> SEQ ID NO 37
<211> LENGTH: 19
<212> TYPE: DNA
<213> ORGANISM: Homo sapiens

<400> SEQUENCE: 37
ctgattcatt acaaggtgg                                                    19

<210> SEQ ID NO 38
<211> LENGTH: 30
<212> TYPE: DNA
<213> ORGANISM: Homo sapiens

<400> SEQUENCE: 38
cactgtgttt tttcataaaa cacctgaaac                                        30

<210> SEQ ID NO 39
<211> LENGTH: 25
<212> TYPE: DNA
<213> ORGANISM: Homo sapiens

<400> SEQUENCE: 39
tggcaagaag tacttggttt gggtc                                             25

<210> SEQ ID NO 40
<211> LENGTH: 28
<212> TYPE: DNA
<213> ORGANISM: Homo sapiens

<400> SEQUENCE: 40
tggagccaaa cattaagtac gtatttca                                          28
```

```
<210> SEQ ID NO 41
<211> LENGTH: 23
<212> TYPE: DNA
<213> ORGANISM: Homo sapiens

<400> SEQUENCE: 41
aaacattaag tacgtatttc aag                                              23

<210> SEQ ID NO 42
<211> LENGTH: 29
<212> TYPE: DNA
<213> ORGANISM: Homo sapiens

<400> SEQUENCE: 42
gcttccatct ctacagggca ccttacttc                                        29

<210> SEQ ID NO 43
<211> LENGTH: 49
<212> TYPE: DNA
<213> ORGANISM: Homo sapiens

<400> SEQUENCE: 43
cattccgaac tgggttttgg tatcagactt tttttgattg gattaaaag                  49

<210> SEQ ID NO 44
<211> LENGTH: 50
<212> TYPE: DNA
<213> ORGANISM: Homo sapiens

<400> SEQUENCE: 44
cacatcgatg tttatcaggg atattggcct aaaattttct ttttttttgtt                50

<210> SEQ ID NO 45
<211> LENGTH: 50
<212> TYPE: DNA
<213> ORGANISM: Homo sapiens

<400> SEQUENCE: 45
gtgtctctgc caggttttgg tatcagaatg atgctggcct cataaaatga                 50

<210> SEQ ID NO 46
<211> LENGTH: 37
<212> TYPE: DNA
<213> ORGANISM: Homo sapiens

<400> SEQUENCE: 46
gttttggtat cagaatgatg ctggcctcat aaaatga                               37

<210> SEQ ID NO 47
<211> LENGTH: 50
<212> TYPE: DNA
<213> ORGANISM: Homo sapiens

<400> SEQUENCE: 47
gttagggagt attccctctt tttctactgt ttggaacagt ttcagaagga                 50

<210> SEQ ID NO 48
<211> LENGTH: 50
<212> TYPE: DNA
<213> ORGANISM: Homo sapiens

<400> SEQUENCE: 48
atggtaccag ctcctctttg tacctctggt agaatgtggc tgtgaatccg                 50
```

```
<210> SEQ ID NO 49
<211> LENGTH: 50
<212> TYPE: DNA
<213> ORGANISM: Homo sapiens

<400> SEQUENCE: 49
tctggtcctg gactttttttt gattggtagg ctattaatta ctgcctcaat          50

<210> SEQ ID NO 50
<211> LENGTH: 25
<212> TYPE: DNA
<213> ORGANISM: Homo sapiens

<400> SEQUENCE: 50
tctggtcctg gactttttttt gattg                                     25
```

SPLICE VARIANTS OF HUMAN IL-23 RECEPTOR (IL-23R) MRNA AND USE OF A Δ9 ISOFORM IN PREDICTING INFLAMMATORY BOWEL DISEASES

CROSS-REFERENCE TO RELATED APPLICATIONS

This application is a division of application Ser. No. 12/386,146, filed Apr. 14 2009 now U.S. Pat. No. 8,206,925, which claims the benefit under 35 U.S.C. §119(e), of U.S. Provisional Application Nos. 61/124,092 filed Apr. 14, 2008, 61/124,099 filed Apr. 14, 2008, 61/124,367 filed Apr. 14, 2008, and 61/124,355 filed Apr. 16, 2008, the entire disclosures of which are hereby incorporated by reference in their entirety.

FIELD OF THE INVENTION

The present invention generally relates to cloning of mRNA splice variants of a cytokine receptor. Specifically, the present invention is directed to novel mRNA splice variants of interleukin 23 receptor (IL-23R) in human. There is disclosed the use of a splice IL-23R mRNA variant (Δ9 isoform) in predicting inflammatory bowel diseases, such as Crohn's disease.

BACKGROUND OF THE INVENTION

Crohn's disease represents one of the inflammatory bowel diseases, and it affects 1.4 million Americans. Crohn's disease causes breaks in the lining of the small and large intestines and can affect the entire digestive system. Ulcerative colitis is usually restricted to the large intestine and involves inflammation of more superficial layers of the bowel lining, while Crohn's also affects deeper layers. The disease likely increases the risk of cancer in the area of inflammation. For example, individuals with Crohn's disease involving the small bowel are at higher risk for small intestinal cancer. Similarly, people with Crohn's colitis have a relative risk of 5.6 for developing colon cancer. In addition to intestinal problems—cramps, diarrhea and rectal bleeding—Crohn's can also cause painful skin ulcers, eye conditions that can interfere with vision, inflammation of the liver and arthritis, among other complications. Symptoms usually begin in adolescence or young adulthood and then intermittently flare up.

There are treatments for Crohn's, but no cure. Anti-inflammatory drugs, immune system suppressants, antibiotics and surgery are all used, with varying degrees of success. Most treatments have side effects that can range from trivial to debilitating.

The etiology of Crohn's diseases is complex and multifactorial. It has a strong genetic link; for example, the disease runs in families and those with a sibling with the disease are 30 times more likely to develop it than the normal population. Ethnic background may be a risk factor. Mutations in the CARD15 gene (also known as the NOD2 gene) have been suggested to associate with Crohn's disease. The frequency of variations in the gene for a receptor of a cytokine (interleukin-23, or IL-23) was significantly different in people with Crohn's disease as compared to that with healthy people. Therapy targeting p40, a subunit of IL-23, can inhibit the activity of IL-23 in Crohn's disease (Mannon P, N. Engl. J. Med. 351:2069, 2004). Screening for colon cancer with colonoscopy is recommended for anyone who has had Crohn's colitis for at least eight years.

Interleukin-23 is a newly identified cytokine and it belongs to the IL-6 superfamily. IL-23 is composed of a common p40 subunit (shared with IL-12) and an IL-23 specific p19 subunit. The IL-23 receptor is a heterodimeric complex that consists of the common IL-12Rβ1 chain and a unique IL-23Rα chain, which is the main signaling chain of the receptor [Parham et al. 2002].

Abnormalities in the immune system and secretion of various cytokines have also been invoked as being causes of Crohn's disease. Crohn's disease is thought to be an autoimmune disease, with inflammation stimulated by an over-active Th17 cytokine response. An increasing body of evidence also exists in favor of the hypothesis that Crohn's disease may results from an impaired innate immunity, which may be due to (at least in part) to impaired cytokine secretion by macrophages.

The human IL-23R gene is composed of at least 12 exons flanking a 92.5 kb genomic region within chromosome 1p32.1-p31.2. The mRNA of IL-23R is 2.8 kb long and comprises 11 exons (NM_144701). The transcribed mRNA is translated into a protein of 629 amino acids, resulting in a type-I transmembrane protein which contains a signal peptide, an N-terminal fibronectin III-like domain and a 252 residue cytoplasmic domain with three potential tyrosine phosphorylation sites [Parham et al. 2002]. IL-23R is a member of the hemopoietin receptor superfamily. The IL-23 receptor complex can be selectively expressed on the "Th17" subset of $CD4^+$ T lymphocytes and low levels of IL-23R expression have also been detected on monocytes, macrophages and dendritic cells [Parham et al, 2002]. The function of IL-23 has not been clearly defined, although it has been reported to work in tandem with interleukin-6 (IL-6) and interleukin-21 (IL-21) to drive the proliferation and functional development of $CD4^+$ Th17 cells. Binding of IL-23 to its receptor activates STAT3 and IL-17 production is subsequently induced.

There are structural and functional similarities between IL-23/IL-23R and IL-12/IL-12R signaling, both may have possible related regulatory functions in T cell development, and T cell-mediated immune responses which bridge innate and adaptive immunity. IL-12/IL-12R signaling plays a pivotal role in Th1 cell responses by promoting IFN-γ production during infection; and IL-23/IL-23R signaling is the central molecule of the Th17 cell differentiation by up-regulation IL-17 production in inflammatory and auto-immune responses. The importance of IL-23R in controlling innate immunity via Th17 cells may underscore why the IL-23R gene also has been demonstrated to confer susceptibility to several autoimmune diseases, including psoriasis [Capon et al. 2007; Nair et al. 2008], ankylosing spondylitis [Rueda et al. 2008], multiple sclerosis [Illes et al. 2008; Roos et al. 2007; Begovich et al. 2007] and inflammatory bowel diseases (both Crohn's Disease and/or ulcerative colitis) [Duerr et al. 2006; Raelson et al. 2007]. In addition, a separate study by the Wellcome Trust Case Control Consortium and the Australo-Anglo-American Spondylitis Consortium [2007] found evidence to suggest that IL-23R may be a common susceptibility factor for the major 'sero-negative' diseases.

Zhang et al. have reported a number of IL-23R splice variants for IL-23R mRNA and some variants are reported in cancer cells. No information exists, however, if any splice variant(s) may be associated with inflammatory diseases, let alone inflammatory bowel diseases such as Crohn's disease.

A recent genome wide association (GWA) study first demonstrated that variants of IL-23R is one of the genetic factors contributing to Crohn's disease. Among the SNPs within IL-23R, one (rs11209026, R381Q) is negatively associated with Crohn's disease, which implies that the Q allele may play a protective role in the pathogenesis of Crohn's diseases [Duerr et al. 2007]. Afterwards, more GWA studies support this R/Q SNP to other diseases from different populations [Jacobs et al, 2007].

There is a continuing need to identify novel IL-23R polymorphic elements and novel markers for predicting inflammatory bowel diseases in humans.

SUMMARY OF THE INVENTION

The present invention provides twenty-five (25) splice variants of IL-23R mRNA and the corresponding deduced amino acid sequences.

In one aspect, the present invention provides an isolated variant of IL-23R mRNA. There is disclosed a total of 25 IL-23R mRNA variants.

In one aspect, the present invention provides an isolated variant of IL-23R full-length mRNA that is devoid of exon 9. The Δ9 IL-23R variant having a nucleotide sequence set forth in SEQ ID NO: 6.

In one aspect, the present invention provides a method of quantifying an IL-23R mRNA variant in a biological sample, comprising the steps of: (a) obtaining a biological sample from a subject; (b) isolating a RNA from said biological sample; and (c) quantifying an IL-23R mRNA variant level in said isolated RNA. Preferably, the quantifying step is performed using qPCR.

In one aspect, the present invention provides a method of quantifying an IL-23R mRNA variant in a biological sample, said method comprising the steps of: (a) isolating a mRNA from a biological sample; (b) preparing a cDNA from said isolated mRNA; (c) amplifying a portion of said cDNA corresponding to exon 9, wherein said method utilizes quantitative competitive PCR assay to determine a relative quantitative level of a IL-23R mRNA variant in said biological sample. The biological sample is derived from a human. Preferably, the biological sample is a cell, tissue, or biological fluid. The tissue may be colon tissue and the biological sample may be whole blood.

In one aspect, the amplify step is performed using a forward primer and a reverse primer, said forward primer having a nucleotide sequence set forth in SEQ ID NO: 26 or SEQ ID NO: 27, and said reverse primer having a nucleotide sequence set forth in SEQ ID NO: 28.

In one aspect, the present invention provides a method of predicting an increased risk of inflammatory bowel disease in a human subject, said method comprising the steps of: (a) obtaining a biological sample from a human subject; (b) performing a quantitative PCR using a set of primer, said primer set having SEQ ID NO:29 and SEQ ID NO:30 or SEQ ID NO:31 and SEQ ID NO:32; and (c) predicting an increased risk of inflammatory bowel disease if the result of said PCR reveals a decrease in Δ9 isoform of IL-23R. The inflammatory bowel disease may be ulcerative colitis or Crohn's disease. Preferably, the inflammatory bowel disease is Crohn's disease.

In one aspect, the present invention provides a method of predicting a bowel inflammation, comprising the steps of: (a) obtaining a biological sample from a human subject; (b) isolating RNA from said biological sample; (c) quantifying Δ9 IL-23R level in said isolated RNA using qPCR; and (d) predicting the presence of a bowel inflammation if there is a decreased Δ9 IL-23R in level in said subject when compared to a control subject. Preferably, the qPCR is performed using a set of primer, said primer set having a SEQ ID NO: 29 and SEQ ID NO:30 or SEQ ID NO:31 and SEQ ID NO:32.

BRIEF DESCRIPTION OF THE DRAWINGS

FIG. 3 depicts the predicted IL-23R protein expression pattern from the splice deletion variants discovered in the present invention. Each box represent the protein encoded by each exon. The grey boxes indicated the untranslated region (UTR), and the 5'-UTR locates in exon 1 and part of exon 2; the 3'-UTR locates in the second half of exon 11. The signal peptide is encoded in exon 2. The translation start site (ATG) is indicated. The mature extracellular domain is encoded within the exons spanning from exon 3 to exon 8. The single transmembrane spanning region is encoded within exon 9. The intracellular domain is spanning from exon 10 to exon 11. The ATG indicates the translation start codon and the "STOP" indicates the stop codon encoded in each of the IL-23R splice variants. Several different splice variants causing the same predicted protein structures are grouped. The predicted biological function from the variant mRNAs are categorized into four possible groups which are short premature IL-23R extracellular peptide, which may or may not be likely NMD pathway candidates; soluble forms of IL-23Rα without transmembrane/intracellular domain; truncated IL-23R extracellular region with intact transmembrane/intracellular domain; and the dominant negative form of IL-23R with a truncated intracellular domain.

FIG. 11 depicts the quantitative PCR assay for an IL-23R splice variant (i.e., Δ9 IL-23R isoform): (a) amplification plot of Δ9 in real-time PCR, (b) dissociation curve of Δ9, and (c) standard curve of Δ9. The PCR efficiency (E) is calculated from the slope of the standard curve.

FIG. 17 summarizes the relative expression of Δ9 in the inflamed and non-inflamed areas of colon from active crohn's disease patients. The relative expression level of Δ9 was decreased in the inflamed area of colon when compared to the non-inflamed area.

FIG. 19 summarizes the analysis of the relative expression of Δ9 in PBMC. The relative expression level of Δ9 was reduced in the PBMC isolated from the active Crohn's patient when compared to PBMC isolated from the healthy donor.

DETAILED DESCRIPTION OF THE INVENTION

Figure 1:
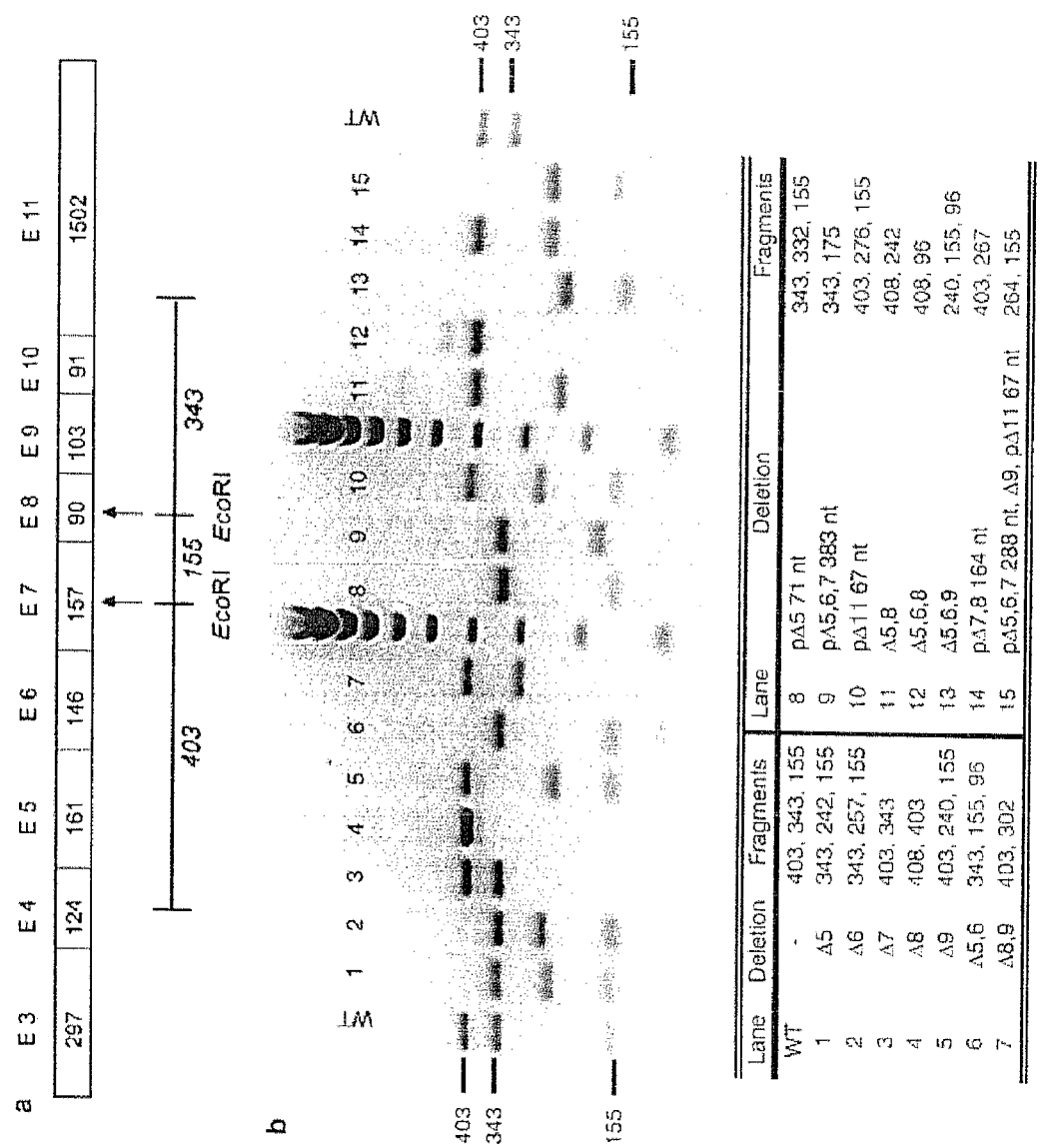
FIG. 1 depicts a representative panel of splice variants RT-PCR products digested with EcoRI endonuclease. (a) schematic view of the IL-23R mRNA. The size of PCR fragment generated by IL-23R primer pair P5/P6 is 901 bp. Two endogenous EcoRI recognition sites within exon 7 and exon 8 digest the IL-23R P5/P6 PCR fragments into three DNA pieces: exon 4-7 (403 bp), exon 7-8 (155 bp) and exon 8-11 (343 bp). (b) 15 different splice variant digested with EcoRI and resolved in 2% agarose gel. Lane 1-7: the splicing variants involved with simple exon skipping. Lane 8-10: the splicing variants involved with partial exon skipping. Lane 11-15: the splicing variants involved with compound exon(s) skipping events. The information of the exon deleted in each variant and the predicted digested fragment sizes is summarized below.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments of the modifications thereof are contemplated as falling within the scope of the present invention and equivalents thereto. All publications, patent applications, patents, GenBank accession nos., and other references mentioned herein are incorporated by reference in their entirety.

Definitions: Various terms used throughout this specification shall have the definitions set out herein.

The term "isolated" (when used in the context of polypeptides and nucleic acids) means that the polypeptides or nucleic acids are essentially free of other substances with which they may be found in vivo. It refers to materials removed from their original environment (e.g., the natural environment if it is naturally occurring).

The term "intron" refers to regions of a primary mRNA transcript that are not included in a finished mRNA. Introns are also known as "intervening sequences."

The term "exon" refers to a region of a primary transcript that remains in the mature mRNA when it reaches the cytoplasm. The exons are "spliced" together to form the mature mRNA sequence.

The term "intron-exon junction" refers to a "splice site" with the 5' side of the junction often called the "5' splice site," or "splice donor site" and the 3' side the "3' splice site" or "splice acceptor site."

The term "cryptic" when used in connection with splice sites refers to those that are less often used but may be used when the "usual" splice site is blocked or unavailable.

The term "alternative splicing" refers to the use of various combinations of exons, often results in multiple mRNA transcripts from a single gene.

The term "primer" refers to a nucleotide sequence that can be extended by template-directed polymerization. For the purpose of this application, the term "nucleotide sequence" is intended to include DNA or modification thereof.

The term "PCR" refers to multiple amplification cycles that selectively amplify a target nucleic acid species. A full description of the PCR process, and common variations thereof, such as quantitative PCR (QPCR), real-time PCR), reverse transcription PCR (RT-PCR) and quantitative reverse transcription PCR (qRT-PCR) are well described in the art. A typical PCR reaction includes three steps: (i) a denaturing step in which a target nucleic acid is denatured; (ii) an annealing step in which a set of PCR primers (forward and backward primers) anneal to complementary DNA strands; and (iii) an elongation step in which a thermostable DNA polymerase elongates the primers. By repeating this step multiple times, a DNA fragment is amplified to produce an amplicon, corresponding to the target DNA sequence.

The term "qRT-PCR" refers to quantitative reverse transcription polymerase chain reaction. qRT-PCR is used to amplify and simultaneously quantify a targeted cDNA molecule. It enables both detection and quantification of a specific sequence in a cDNA pool, such as the Δ9 variant of the IL-23R.

The term "real-time PCR" may use DNA-binding dye to bind to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

The term "biological sample" may include, but is not limited to, whole blood, cells (e.g., peripheral blood mononuclear cells) or tissues (e.g., colon tissues). Extraction of nucleic acids (such as mRNA) from biological samples is known to those skilled in the art. Exemplary methods include, but not limited to, guanidinium thiocyanate, guanidine hydrochloride, phenol-chloroform extraction and the like.

The term "inflammatory bowel disease" refers generally to an inflammatory disease of the digestive tract in a human. It is intended to encompass inflammatory conditions of the large intestine and small intestine. Exemplary type of inflammatory bowel disease includes Crohn's disease and ulcerative colitis. Other minor forms of inflammatory bowel diseases include collagenous colitis, lymphocytic colitis, ischaemic colitis, diversion colitis, Bahcet's syndrome, infective colitis, and indeterminate colitis, all of these forms are characterized by having an inflammatory condition.

The practice of the present invention will employ, unless otherwise indicated, various techniques of molecular biology, microbiology, and biochemistry, which are generally within the skill of the art. Such techniques are explained in the literature, such as, "Molecular Cloning: A Laboratory Manual", 2nd edition (Sambrook et al., 1989); "Oligonucleotide Synthesis" (M. J. Gait, ed., 1984); "Current Protocols in Molecular Biology" (F. M. Ausubel et al., eds., 1987); and "PCR: The Polymerase Chain Reaction" (Mullis et al., eds., 1994).

In one embodiment, the present invention provides novel IL-23R polymorphic mRNA variants. The present discovery is directed to a range of novel splice variants of IL-23R transcripts, and greatly extends an earlier study by Zhang et al. in 2006. Zhang has shown a number of IL-23R splice variants present in normal lymphoid cell lines and human tumor cells. Six (6) spice isoforms are shown to be present in cells through alternative splicing. IL-23R1 and IL-23R3 expression is low in peripheral blood cells, and IL-23R2 and ILR4 are present in lung adenocarcinoma cells. Zhang's observation is thus limited to normal lymphoid cells and human tumor cells and has not been confirmed. Given the unpredictable nature of cytokine molecules and their molecular gene functions, the role of additional novel IL-23R splice isoforms and their role in infectious or inflammatory diseases such as inflammatory bowel diseases are presently unknown.

A previous report by Zhang et al. (2006) described a total of six (6) deletion splice variants of the human IL-23 receptor mRNA. (See, FIG. 3 of Zhang). Confusingly, they have used a non-standard 12-exon nomenclature. In the present invention, there is provided the internationally-recognized 11-exon one, derived using the Genbank reference sequence for the human IL-23 receptor alpha chain, NM_144701. When compared between Zhang and the present discovery, Zhang's "exon 10" corresponds to "exon 9" of the present invention.

In accordance with the present invention, the deletion variant wherein exon 9 is absence ("Δ9") having a nucleotide sequence set forth in SEQ ID NO: 6 of the present invention. Previous report did not disclose Δ9. While three of Zhang's variants (i.e., IL-23R3, IL-23R5 & IL-23R6) did not contain exon 9 (i.e., the "exon 10"), this was always in combination with one or more additional whole or partial deletions. Accordingly, the present invention provides for the first time an isolated IL-23 splice deletion variant lacking exon 9 (i.e., "Δ9 alone" variant). None of the "exon 10" deletion variants described by Zhang was discovered in our investigations that underpin the present invention.

It is noteworthy that variant "Δ9" (i.e., SEQ ID NO: 6) of the present invention differs from the "exon 10" deletion variants of Zhang. When referenced to the wild-type IL-23R nucleotide sequence (i.e., Genbank sequence NM_144701), the variant Δ9 (i.e., SEQ ID NO: 6) of the present invention contains the amino acid arginine (Arg, R) at the position 302 and the nucleotide thymidine (T) at base 1687 (Genebank AM990318). This represents a unique genetic variant of the IL-23 receptor, distinct and distinguishable from the IL-23R3 (missing "exon 7" and "exon 10") of Zhang, which contains the amino acid glycine (Gly, G) and the nucleotide cytosine (C) at the same positions (Genbank AY937253). Simply put, the present invention provides a novel Δ9 isoform of IL-23R splice variant.

In another embodiment, the present invention provides an understanding and utility of these variants in predicting a pathogenesis role of IL-23R in human Crohn's disease. The present invention relates to IL-23/IL-17 pathway and can be extended to other autoimmune diseases. Accordingly, the present invention provides a better understanding for possible pathogenic mechanisms of IL-23R and their contribution to disease susceptibility.

In another embodiment, the present invention provides a quantitative PCR assay to measure levels of alternative mRNA isoforms of IL-23R in human. This protocol provides a tool for identifying in a quantitative manner of the IL-23R mRNA variants. Specifically, the protocol permits predicting if an individual is at risk of inflammatory bowel diseases (such as Crohn's disease) by monitoring a IL-23R isoform (i.e., Δ9) in tissues.

In a preferred embodiment, the present invention provides a method of quantifying Δ9 IL-23R isoform, comprising the steps of: (a) obtaining a biological sample from a subject; (b) isolating RNA from said biological sample; and (c) quantifying Δ9 IL-23R level in said isolated RNA using qPCR.

Primers for quantitative PCR amplification of Δ9 IL-23R sequence can be designed based on the sequence of the target sequence, in accordance with standard procedures. Design and synthesis of these primers can be modified based on the abilities of those of skill in the art. Primers function to anneal and amplify Δ9 IL-23R unique target sequence and as a generator of a signal for detection and monitoring of an amplification reaction.

In the mRNA of Δ9 IL-23R isoform, exon 9 (i.e., nucleotides 1131-1233 of GenBank Sequence NM_144701) is specifically deleted. This deletion results in the connection of exon 8 (i.e., nucleotide 1041-1130 of GenBank Sequence NM_144701) directly to exon 10 (i.e., nucleotide 1234-1324 of GenBank Sequence NM_144701).

Within the context of the present invention, precise sequence of a particular primer is not critical. In accordance with the present invention, primers are typically used in pairs to amplify unique genomic sequences (e.g., such as Δ9 IL-23R). Thus, according to an embodiment of the invention, primer pairs that function to amplify this target region of the gene is suitable for use in the invention. Primer pairs may be designed by one of ordinary skill in the art without undue experimentation. Generally, forward and reverse primers for the Δ9 IL-23R isoform is designed across the junction of exon 8 (i.e., nucleotides 1110-1130 of GenBank Sequence NM_144701) and the junction of exon 10 (i.e., nucleotide 1234-1250 of GenBank Sequence NM_144701). These primers can specifically amplify the Δ9 IL-23R isoform.

In an exemplary embodiment, the forward primer for the Δ9 specific isoform having a nucleotide sequence set forth in SEQ ID NO: 31 (5' GGCACCTTACTTCTGGATTAAAAG 3'). In this forward primer, the first 15 nucleotides correspond to the exon 8 from nucleotide 1116-1130 of GenBank Sequence NM_14470), and the last 9 nucleotides of this primer correspond to the exon 10 from nucleotide 1234-1243 of GenBank Sequence NM_144701. In an exemplary embodiment, the reverse primer for the Δ9 specific isoform having a nucleotide sequence set forth in SEQ ID NO: 32 (5' GGACCTGCTCACTGGAATTA 3'). In this reverse primer, the nucleotides correspond to the exon 11 from nucleotide 1348-1368 of GenBank Sequence NM_144701.

Probes may be provided in addition to primers. Probes that can be used for detection of amplification of the unique genomic sequences (e.g., TaqMan® probes or molecular beacon) can be designed to hybridize to a sequence between the two amplification primers, preferably within 5-15 bases of one of the primer binding sites. Design and synthesis of such probes is well within the abilities of those of skill in the art. Typically, probes are present in reaction mixtures in conjunction with primers or sets of primers for a particular amplification reaction, whether it be an amplification of a unique a target sequence. However, probes may be provided as separate components, which are separate from the primer(s) or other components of a reaction mixture.

The primers and probes are designed to have the typical size for primers and probes for use in PCR reactions. In general, the primers are relatively short (about 10-30 bases in length) oligonucleotides, while the probes (e.g., TaqMan® probes) may be from about 15-35 bases in length. The primers and probes are designed through a process that includes identification of unique sequences on a target nucleic acid, designing short oligonucleotides to amplify or detect those sequences, and synthesizing the oligonucleotides. Several characteristics may be taken into consideration when designing the primers and probe: e.g., the probe melting temperature should be higher than the primer melting temperatures, and the distance between the 3'-end of one primer and the 5'-end of the probe may be less than 8 nucleotides. One of skill in the art is well aware of these considerations and characteristics, and may select among them to provide suitable primers and probes according to the invention without undue or excessive experimentation. Protocols for synthesis of oligonucleotides are known to those skilled in the art.

In one embodiment, the present invention provides an assay employing quantitative real-time RT-PCR, which is an accurate, precise, high throughput assay. Real-time PCR automates the process of relative RT-PCR by quantitating reaction products for each sample in every cycle. In some embodiments real-time PCR systems rely upon the detection and quantitation of a fluorescent reporter, the signal of which increases in direct proportion to the amount of PCR product in a reaction. In the simplest and most economical format, that reporter is the double-strand DNA-specific dye SYBR® Green (Molecular Probes). SYBR® Green binds double-stranded DNA, and upon excitation emits light. Thus, as a PCR product accumulates, fluorescence increases.

The SYBR® Green (Molecular Probes, Eugene, Oreg.) system is a simple and cost-effective way to detect and quantify PCR products in real time. The SYBR® Green dye binds, in a sequence non-specific manner, to double-stranded nucleic acids. It thus can be used for detection and quantitation of double-stranded products produced from single-stranded templates (e.g., mRNA). In this case, the SYBR binds to amplicons (double stranded DNA) generated by gene specific primer in the real-time PCR. The fluorescent intensity represents the amount of amplicons. The specificity of this assay was depending on the primer specificity during PCR amplification. Other detectable probes and primers, such as Sunrise™ primers, amplifluor probes, and DNAzymes, may be optimized for quantitative detection of amplification products.

Two alternatives to SYBR® Green are (i) TaqMan® (Applied Biosystems, Foster City, Calif.) and (ii) molecular beacons, both of which are hybridization probes relying on fluorescence resonance energy transfer (FRET) for quantitation. Both of these alternatives can be used to quantitatively measure Δ9 IL-23R isoform mRNA level. TaqMan® Probes are oligonucleotides that contain a fluorescent dye, typically on the 5' base, and a quenching dye, typically located on the 3' base. More specifically, for TaqMan® probes, when the probe is intact, the quencher quenches the signal produced by the fluorescent label. However, upon binding of the probe to the target sequence and subsequent digestion of the probe by the 5'-3' exonuclease activity of a polymerase, such as Taq polymerase, the fluorescent moiety is released from the quencher moiety, and a detectable signal, which is proportional to the amount of target nucleic acid being produced, is produced and can be monitored. In one embodiment, Taq polymerase are used in qRT-PCR due to its 5'-3' exonuclease activity and it changes the fluorescence of the probes and allows amplification of Δ9 IL-23R mRNA. TaqMan® probes rely on degradation by a polymerase to generate a detectable signal, whilst Scorpions and Molecular Beacons rely on opening of a hairpin structure to provide a detectable signal. Like TaqMan® probes, Scorpion probes contain both a fluorescent moiety and quenching moiety on a single probe. However, unlike TaqMan® probes, Scorpions are not degraded during the amplification reaction. Rather, they are designed as primers for amplification reactions. Scorpion primers are designed to form hairpin structures in solution, which causes the fluorescent moiety and the quenching moiety to be in close proximity. Binding of the primers to target nucleic acids unfolds the hairpin structure and moves the quenching moiety a sufficient distance away from the fluorescent moiety that detectable fluorescence is emitted.

In one embodiment, the present invention provides a method of using fluorescent probe to specifically bind to the connection region of the exon 8 (i.e., nucleotide 1110-1130 of the GenBank sequence NM_144701) and exon 10 (i.e., nucleotide 1234-1250 of the GenBank sequence NM_144701). Therefore, the probe specifically recognizes the IL-23R mRNA when exon 9 is deleted (i.e., the Δ9 isoform). Because the probe is fluorescent labeled at one end, when the probe does not bind to its complementary sequence (i.e., free soluble form), the fluorescent signal is disrupted by the quenching dye. No fluorescent signal is observed. However, when the probe binds to its complementary sequence (i.e., bound form), the fluorescent dye is displayed away from the quenching dye, resulting in a fluorescent signal. Accordingly, the intensity of fluorescent signal is used to measure the level of the amplicons.

In one embodiment, the present invention provides a method of using TaqMan qRT-PCR. TaqMan probes may be used with Quanta's OneStep qRT PCR buffer. TaqMan probes only fluoresce when the target sequence of the probe is amplified by the qRT PCR. The probe, consisting of a reporter dye and quencher, binds a target sequence and is subsequently cleaved by DNA Polymerase during the extension step of the qRT-PCR, releasing the dye from its quencher and emitting fluorescence. This method produced high sensitivity and specificity levels acceptable in a clinical setting.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. When a molecular beacon hybridizes to a target, the fluorescent dye and quencher are separated, FRET does not occur, and the fluorescent dye emits light upon irradiation.

The present invention also provides a method of predicting of bowel inflammation, comprising the steps of: (a) obtaining a biological sample from a subject; (b) isolating RNA from said biological sample; (c) quantifying Δ9 IL-23R level in said isolated RNA using qPCR; and (d) predicting an increased risk of bowel inflammation if there is a decreased Δ9 IL-23R in level in said subject when compared to a control subject.

In accordance with the present invention, there is disclosed 25 different mRNA splice variants of human IL-23R from activated human leukocytes (including three that were disclosed by Zhang et al. (2006): namely, Δ5, Δ9 and Δ8 plus pΔ11 67 nt). The 22 novel splice variants greatly expand our knowledge of the isoforms of IL-23R at the level of mRNA. The multiple splice variants of IL-23R were not only observed in activated human blood cells. Similar results of the multiple IL-23R splice variants were also observed in the human embryonic kidney cell line (HEK-293T/17) culture and also in the "MegaMan" human transcriptome library (Stratagene). No specific correlations were observed between the isoforms of splice variants and the particular mitogen used for stimulation, nor were we able to identify variants that were preferentially observed between individuals. These data suggest that IL-23R gene expression is very dynamic.

Not wishing to be bound a theory, the present inventors hypothesize that alternative splicing plays an important role in regulating gene expression by generating multiple mRNA transcripts from a single gene in specific spatial/temporal patterns, which greatly expands the proteome information content and flexibility for gene expression. The mechanisms and functional significance of the process, however, are still unclear. IL-23R gene is a recently discovered interleukin receptor, which plays a pivotal role in human autoimmune responses via Th17 pathway. Translated variants of such an important mRNA species may have important modulatory functions on the development or maintenance of autoimmunity in man.

In one embodiment, the present invention provides a total of twenty-five (25) splice forms of IL-23R mRNA. The 25 splice forms include: (1) Δ4 (GenBank Entry No: AM990313) (SEQ ID NO:1), (2) Δ5 (GenBank Entry No: AM990314) (SEQ ID NO:2), (3) Δ6 (GenBank Entry No: 990315) (SEQ ID NO:3), (4) Δ7 (GenBank Entry No: AM990316) (SEQ ID NO:4), (5) Δ8 (GenBank Entry No: AM 990317) (SEQ ID NO:5), (6) Δ9 (GenBank Entry No: AM990318) (SEQ ID NO:6), (7) Δ5,6 (GenBank Entry No: AM990319) (SEQ ID NO:7), (8) Δ6,7 (GenBank Entry No: AM990320) (SEQ ID NO:8), (9) Δ8,9 (GenBank Entry No: AM990321) (SEQ ID NO:9), (10) Δ5,6,7 (GenBank Entry No: AM990322) (SEQ ID NO:10), (11) pΔ5 5 nt (GenBank Entry No: AM990323) (SEQ ID NO:11), (12) pΔ5 71 nt (GenBank Entry No: AM990324) (SEQ ID NO:12), (13) pΔ11 67 nt (GenBank Entry No: AM990325) (SEQ ID NO:13), (14) pΔ5,6,7 (GenBank Entry No: AM990326) (SEQ ID NO:14), (15) Δ5,8 (GenBank Entry No: AM990327) (SEQ ID NO:15), (16) Δ5,9 (GenBank Entry No: AM990328) (SEQ ID NO:16), (17) Δ5,6,8 (GenBank Entry No: AM990329) (SEQ ID NO:17), (18) Δ5,6,9 (GenBank Entry No: AM990330) (SEQ ID NO:18), (19) pΔ7,8; pΔ11 67 nt (GenBank Entry No: AM990331) (SEQ ID NO:19), (20) pΔ 5,6,7; Δ9; pΔ11 67 nt (GenBank Entry No: AM990332) (SEQ ID NO:20), (21) pΔ5, 5 nt; Δ6,7 (GenBank Entry No: AM990333) (SEQ ID NO:21), (22) pΔ5, 71 nt; Δ8,9 (GenBank Entry No: AM990334) (SEQ ID NO:22), (23) Δ8, pΔ11 67 nt (GenBank Entry No: AM990335) (SEQ ID NO:23), (24) pΔ5, 5 nt; Δ+9a (GenBank Entry No: AM990336 (SEQ ID NO:24); and (25) Δ5,9 (GenBank Entry No: AM990337 (SEQ ID NO:25). (See, FIG. 2).

In one embodiment, the present invention provides polypeptides having deduced amino acid corresponding to the 25 spice forms of IL-23R mRNA. The predicted IL-23R proteins include: (1) Δ4 is a protein consists of 123 amino acids, (2) Δ5, Δ5,8, Δ5,9 is a protein consists of 174 amino acids, (3) Δ6 is a protein consists of 218 amino acids, (4) Δ7 is a protein consists of 283 amino acids, (5) Δ8 is a protein consists of 599 amino acids; (6) Δ9 is a protein consists of 356 amino acids, (7) Δ5,6, Δ5,6,8, Δ5,6,9 is a protein consists of 192 amino acids, (8) Δ6,7 is a protein consists of 528 amino acids, (9) Δ8,9 is a protein consists of 326 amino acid, (10) Δ5,6,7 is a protein consists of 174 amino acid, (11) pΔ5 5 nt, pΔ5, 5 nt; Δ6,7; pΔ5, 5 nt; Δ8 is a protein consists of 178 amino acids, (12) pΔ5 71 nt, pΔ5, 71 nt; Δ8,9 is a protein consists of 191 amino acids, (13) pΔ11 67 nt is a protein consists of 414 amino acids, (14) pΔ5,6,7 is a protein consists of 184 amino acid, (15) pΔ7,8; pΔ11 67 nt is a protein consists of 293 amino acids, (16) pΔ5,6,7; Δ9; pΔ11 67 nt is a protein consists of 260, (17) Δ8, pΔ11 67 nt is a protein consists of 384 amino acids. (See, FIG. 3)

In one embodiment, the present invention provides the predicted protein products derived from the 24 IL-23 mRNA variants and they can be categorized into four (4) possible different protein groups:

(i) short premature IL-23R extracellular peptides;
(ii) soluble forms of IL-23R without transmembrane/intracellular domain;
(iii) a full length of IL-23R with truncated extracellular region; and
(iv) a dominant negative form of IL-23R without intracellular signaling components.

Without wishing to be bound by a theory, it is speculated that some of these mRNA may not survive to be translated because of a cellular process that degrades malformed mRNA, known as "non-sense mediated decay (NMD)." The NMD pathway is a post-transcriptional regulation, which is proficient in recognition the "aberrant" mRNA and rapid down-regulate the mRNA. The NMD pathway is triggered by a premature early termination codon located at least 50-55 bp upstream of the 3'-most exon-exon junction (Lewis et al. 2003). More than half (14 out of 24) of the alternative splicing events described in this report are introducing termination codons into the mRNA immediately after the exon(s) that is/are alternatively spliced (See, FIG. 2). Among these fourteen (14) transcripts, it is interesting to note that twelve (12) involve the deletion of part of, or the entire, exon 5 and lead to generate a potential short peptide containing fewer than 60 amino acids (the full length IL-23Rα is 629 amino acids). However, these transcripts are not likely to be translated into protein because their mRNAs are highly likely to be the target for the NMD pathway. It seems it is common to have some alternative transcripts are not translated into protein due to the NMD pathway control mechanism. Overall, it has been estimated that one-third of mRNA alternative transcripts containing premature termination codon are highly likely to be targets of nonsense-mediated mRNA decay. IL-23Rα variants that may be candidates for NMD are annotated in FIG. 2.

In accordance with the present invention, there is provided three (3) functional IL-23R splice mRNA variants. Three splice variants are of interest because of their yielding potentially functional transcripts: Δ7, Δ9, and Δ8,9. These three (3) transcripts are very likely to be translated to various IL-23Rα protein "early termination" variants, resulting in forms that lack the transmembrane and intracellular regions. They have most of, or the entire, extracellular region of the native protein. Since the transmembrane domain does not exist in these transcripts, the proteins translated from these variants are no longer capable of being anchored into the membrane and so are likely secreted from activated cells. In cytokine signaling, soluble cytokine receptors can regulate immune events by acting as agonists or antagonists. The potential soluble receptors generated by our novel exon variants therefore may block IL-23/IL23R signaling activity by acting as "decoy receptors," greatly expanding the complexity of immunological regulation.

The Δ6,7 and Δ8 transcripts are in-frame deletion variants and if translated would have the transmembrane and intracellular signaling elements of the native IL-23 receptor intact. However, parts of the extracellular domain (encoded by exon 6-7 or exon 8, respectively) are absent. These variants have the potential to display altered ligand binding properties in terms of affinity and specificity relative to the wild type and to signal, because of the intact intracellular domain. These changes within the extracellular domain may also introduce different variety of ligand-receptor kinetic interaction and further signal downstream genes in a different manner than the wild type IL-23R in Th17 pathway development.

Two of the alternatively spliced, in-frame IL-23R mRNA transcripts involved the skipping of only the first 67 nucleotides of exon 11 (Δ11 67 nt; Δ8 plus Δ11 67 nt). If translated, these would encode a nonsignaling, truncated protein, containing the complete IL-23Rα extracellular and transmembrane parts, but with a truncated cytoplasmic tail that lacks two out of the three signaling tyrosine residues and their box motifs. These transcripts are very unlikely to be targets of the NMD pathway and could therefore be translated and perhaps expressed. The extracellular region will still likely to interact with the IL-23 ligand, but the normal downstream signaling activity will be halted due to the truncation. These two variant forms may encode dominant negative variants of the IL-23 receptor. It seems the expression of such truncated proteins may act as negative regulators of the IL-23/IL-23R pathway and Th17 development. The compound variant Δ8; Δ11 67 nt may combine these two properties by having both an altered extracelluar region and a non-functional intracellular region.

The present invention provides a great diversity in the mRNA that is transcribed from the human IL-23R gene. Twenty-five (25) variants were observed in human lymphocytes of which twenty-two (22) have not previously been disclosed. Variants were realized according to stimulation by various mitogens or simple exposure to complete cell culture medium over a three-day period. While many of the variants are likely to be destroyed within the cytoplasm, almost half (10/24) are species that may be translated. These novel translation products may represent regulatory moieties that participate in control of Th17 cells and their pro-inflammatory function, perhaps therefore representing an intrinsic protective mechanism against the development of autoimmune disease or other chronic inflammatory disorders.

Accordingly, the present invention has unveiled the molecular heterogeneity of the expression of IL-23R in human leukocytes. The present invention provides new regulatory features in the expression and possibly function of IL-23Rα, which yields new clues for clarifying the pathogenesis of inflammatory diseases, especially in inflammatory bowel diseases.

The following descriptions of particular embodiments and examples are offered by way of illustration and not by way of limitation.

EXPERIMENTAL STUDIES

Example 1

Evidence for Multiple Splice Variant Transcripts of IL-23 R mRNA

IL-23Rα protein is shown to express on T cells, NK cells, monocytes and dendritic cells [Parham et al. 2002]. In our study, we used reverse-transcriptase PCR method and observed a low, if any detectable, level of expression for IL-23R in un-stimulated peripheral blood mononuclear cells (PBMC). In contrast, we detected a significant up-regulation of the IL-23R cDNA in PBMC after mitogen stimulation for 72 hours.

Next, we used forward primer P3 or forward primer P5 in combination with a reverse primer P6 to generate IL-23R amplicons. The predicted sizes were estimated to be 1,234 bp and 901 bp, respectively. We found multiple transcripts with smaller sizes than the expected sizes of the IL-23R amplicons. This observation suggests the potential existence of multiple splice variant transcripts of the IL-23R mRNA in PBMC.

Example 2

Cloning of Multiple Splice Variant Transcripts of IL-23 R mRNA

Based on this observation, we cloned the multiple splice variant transcripts of IL-23R mRNA. Total RT-PCR products were cloned into TOPO-TA vector pCR2.1 (InVitrogen) to identify the variants of each PCR product individually. Colony PCR was first applied using M13 forward and M13 reverse primers located along the sides the TA cloning sites on the vector to initially screen the colonies generating amplicon size smaller than the wild-type IL-23R.

Example 3

Detection and Identification of IL-23R Splice Variants

In this study, both restriction enzyme digestion and sequence analysis were applied to determine different IL-23R splice variants in activated PBMC cells. To distinguish differences in IL-23R cDNA due to splicing, restriction endonuclease digestion was first performed on the cloned PCR products and band sizes were resolved by agarose gel electrophoresis. The digestion was designed to visualize various IL-23R exon skipping as well as partial exon skipping variants.

Two endogenous EcoRI sites within exon 7 and exon 8 of "wild-type" IL-23R mRNA yielded three DNA fragments of clearly differing size, as depicted in FIG. 1.

The EcoRI restriction digestion of IL-23R P5/P6 PCR fragment clones comprised of three DNA pieces: (i) exon 4-7 (403 bp); (ii) exon 7-8 (155 bp); and (iii) exon 8-11 (343 bp), covering the area after the translated signal peptide which is possibly the area containing most of the alternative splicing events (FIG. 1a).

The diversity of the EcoRI digestion pattern suggests highly polymorphic and dynamic splicing activities were present in the mRNAs of IL-23R gene (FIG. 1b). Clones that revealed different digestion patterns after EcoRI digestion described above were then sequenced to define the exact position and nature of these splice events.

Example 4

Identification of Twenty-Five Novel IL-23R mRNA

Figure 2:
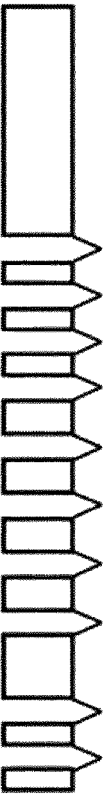
FIG. 2 summaries the 24 different IL-23R splice deletion variants identified in the present invention (the insert variant SEQ ID NO:24 is not shown). Schematic diagrams of IL-23R splice isoforms showing the splicing patterns of the wild-type (GenBank NM_144701) and 24 different variants detected in activated human leukocytes for IL-23R. The shaded boxes represent the deleted ("skipped") exons. The target of NMD (nonsense mediated decay) is determined by a premature early termination codon located at least 50-55 bp upstream of the 3'-most exon-exon junction. Any transcript having its stop codon more than 70 bp upstream of the next splice junction are labeled "Yes," and lower than 50 bp are labeled "No." The transcripts where this falls between 55-70 are labeled a question mark ("?"). In frame deletion and the splicing happening in the last exons are not subjected to the NMD pathway. The Δ4 isoform was revealed from a P3/P6 amplicon and others revealed from P5/P6 amplicons. All the splice variants were deposit in GenBank, as discussed below.
Figure 2:
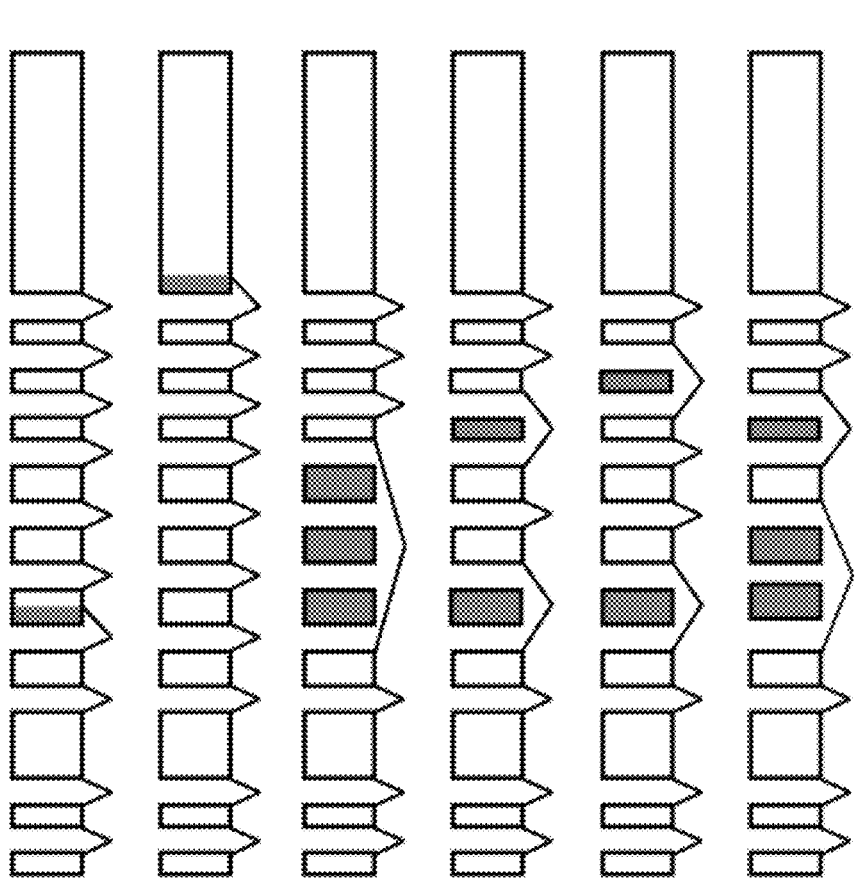
Figure 2:
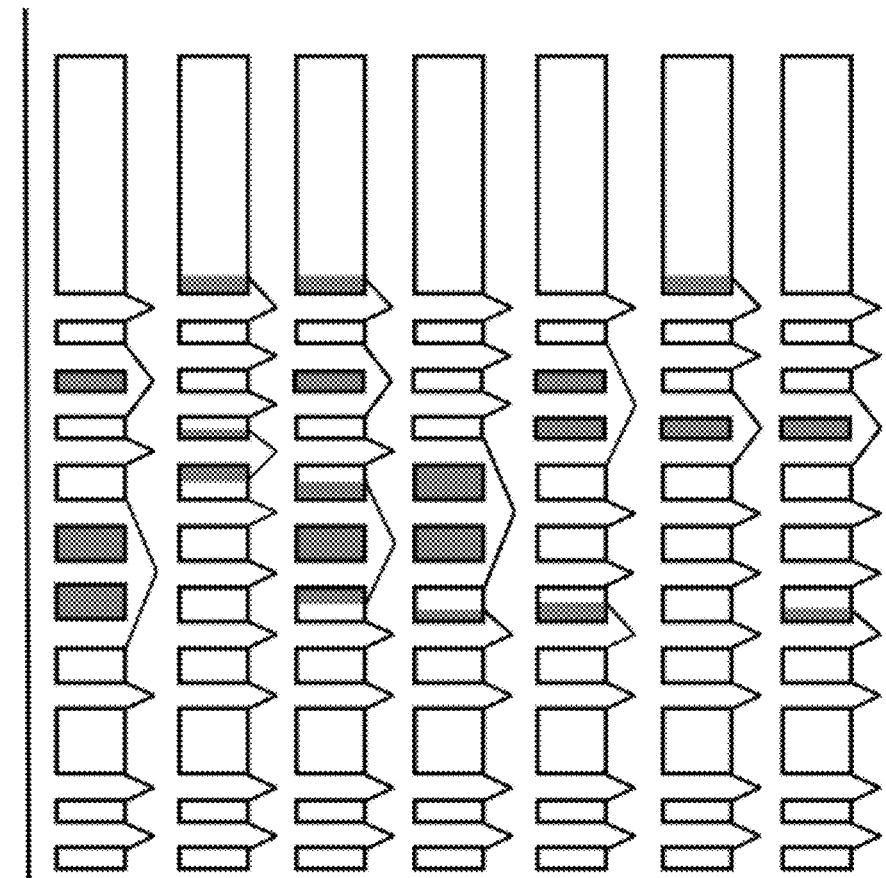

Sequencing of the variant IL-23R fragment cDNA clones identified a total of twenty-five (25) splice IL-23R mRNA variants; namely twenty-one (21) novel IL-23R mRNA splice variants and three (3) (i.e., Δ5: AY937251; Δ9 AY937253; Δ8 and pΔ11 67 nt AY937255) that had previously been identified [Zhang et al. 2006]. The twenty-four (24) IL-23R mRNA splice deletion variants are depicted in FIG. 2, which shows both the simple and compound deletion events discovered in this study.

Example 5

Characterization of Exon Skipping

The exon skipping events can be categorized into: (i) simple deletions, i.e., skipping of complete single exons or consecutive exons (e.g., Δ4; Δ5; Δ6; Δ7; Δ8; Δ9; Δ5,6; Δ6,7; Δ8,9; Δ5,6,7) and (ii) compound deletions, i.e., deletions of partial exons or deletion of non-consecutive exons (e.g., pΔ5 5 nt; pΔ5 71 nt; pΔ 11 67 nt; two different versions of pΔ5-7 and pΔ7-8).

I. Single Exon Deletions

Single exon deletions (of each exon from exon 4 to exon 9) were found in the cDNA pool. In addition, four (4) consecutive-exon skippings (involving more than one exon deletion between exon 5 to exon 9) were also discovered in this study (Δ5,6; Δ6,7; Δ5,6,7; Δ8,9). All of the exon skipping events mainly affected the exons encoding parts of the extracellular region and/or transmembrane domain of IL-23Rα, but not the intracellular domain.

II. Multiple Exon Skipping

The 14 simple exon skipping events are shown in FIG. 2, ten more splicing events have been identified that involved multiple exon skipping events. In these compound-exon skipping transcripts, several splicing events were evident from the pre-mRNA processing (FIG. 2). These compound splicing events include the skipping of combinations of complete exons (Δ5,8; Δ5,9; Δ5,6,8; Δ5,6,9) and combinations of the whole exon skipping and partial exon deletion (pΔ5 5 nt plus Δ8; pΔ5 5 nt plus Δ6,7; pΔ5 71 nt plus Δ8,9; Δ8 plus pΔ11 67 nt; pΔ7,8 plus pΔ11 67 nt and pΔ5,6,7 plus Δ9 plus pΔ11 67 nt). Among these 10 mRNA transcripts, the most complicated one involved three individual splicing events in one transcript. These multiple exon skipping events all involved the entire or part deletion of exon 5/6 and exon 8/9, which implies that the skipping of these exons are common events in the pre-mRNA processing. In addition, the only intracellular exon skipping event, pΔ1167 nt, repetitively occurred with other splice events, also emphasizing its probable importance in pre-mRNA processing of the IL-23R transcript.

The results from the intensive screening of the IL-23R splice variants greatly expand the knowledge of varied IL-23R gene expression in activated human leukocytes. The EcoRI endonuclease digestion results from a selectively panel of 16 out of the 24 different splice variants demonstrated in FIG. 1B, offers an effective and quick method to distinguish different splice variants.

In the IL-23R transcript variants we obtained from human activated leukocytes, most were discovered repeatedly in different conditions of mitogen stimulation; this implies that specific splice variants do not result from different stimuli. However, some of variants were detected only once in the screening implying the splicing events are rare and the transcript is scarce among the cDNA pool.

Example 6

Unusual Splice Sites Usage in IL-23R Splice Variants

I. Partial Exon Deletions

As mentioned above, six partial exon deletion events, of which five were previously unknown, were identified in this study (pΔ11 67 nt+Δ8 deletion, [Zhang et al. 2006]). FIG. 2 depicts these six alternative splice events that involve partial exon deletions instead of the skipping of complete exons. The splice sites used are shown in Table 1. Three of these variants (pΔ5 5 nt, pΔ5 71 nt and pΔ11 67 nt) still keep their original splicing donor site (GT) in the boundary of exon and intron but utilize the next possible legitimate splice acceptor sites (5'-AG) within the exon in the immediate vicinity area, instead of the original ones. These three partial deletion events all cause out-of-frame translation and furthermore, introduce stop codons into the transcripts after the alternative splicing, thereby introducing an early termination of protein translation.

II. Legitimate Spice Sites

The splicing events of the other three variants are much more complicated. The partial deletion pΔ7,8 used a pair of legitimate splice sites (5'-GT/AG-3') within exon 7 and exon 8 to execute a proper splicing event causing a 164 bp deletion and an out-of-frame amino acid change. For the remaining two variants, not only is none of the original splice donor/acceptor sites utilized, but those that are used are very atypical (Table 1). No legitimate splice site pairs could be identified in these two transcripts (involving partial deletion exon 5 to exon 7). Although these two atypical splicing events both occurred within exon 5 and exon 7, causing the entire exon 6 and part of exon 5 and 7 to be deleted, the splicing points utilized in these two transcripts are not the same. The intron area between exon 5/6 and exon 6/7 were searched intensively for any possible cryptic exon events that may have caused these two very atypical alternative splicings, but none was found. No similar sequences were observed within these two intron areas to offer a legitimate set of possible splice donor/acceptor site pairs to fit the (5'-GT/AG-3') rule, thus it is unlikely that (a) cryptic exon(s) within the intron may be involved with these splice events (data not shown).

Example 7

Translation Potential of the IL-23Rα Splice Variants

The predicted protein sequences translated from these variant spliced transcripts are summarized in FIG. 3. A majority of these variants introduce early termination codons into the open reading frames immediately after the alternative splicing event(s) occurred, which may produce premature proteins with only short peptides of IL-23Rα. Four possible IL-23Rα expression patterns predicted from the splice variants can be defined:

I. Short premature IL-23Rα extracellular peptides;
II. Soluble forms of IL-23Rα without transmembrane or intracellular domains;
III. A structurally complete IL-23Rα with a truncated extracellular region; and
IV. A dominant negative form of IL-23Rα without its intracellular signaling components.

All different forms of the IL-23Rα variants, except the short premature IL-23Rα extracellular domain, may possess different biological functions if they can be translated into protein from the mRNA. Five of these transcripts are potentially able to be encoded the soluble forms of IL-23Rα without the transmembrane and intracellular domains and with various truncations of the extracellular region. The change of extracellular region may alter the ligand-receptor binding specificity or affinity and the lack of transmembrane domain may cause the protein to be secreted from the cells instead of anchoring itself in the membrane.

Two transcripts are in-frame deletions that keep the transmembrane/intracellular domains intact, but change the extracellular regions. These isoforms still keep the ability to initiate downstream signaling, however the change of extracellular domain may again vary the ligand binding ability and specificity. Finally, two isoforms containing the partial deletion of exon 11 may inhibit or prevent receptor signaling because of the lack of two out of the three tyrosine activation motifs [Parham et al. 2002].

Example 8

Identification of Cryptic Exon 9a

Figure 4:
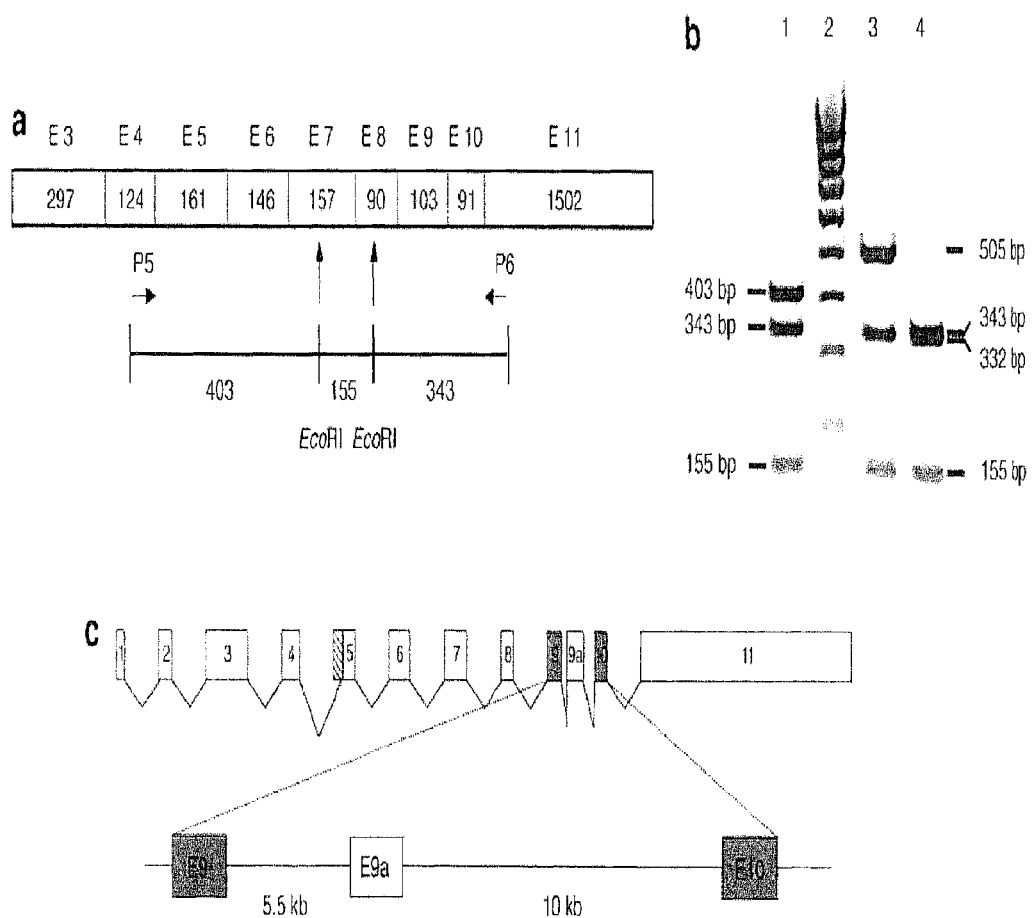
FIG. 4 depicts the characterization of the exon 9a insertion variant of IL-23R (SEQ ID NO: 24): (a) primer set and digestion sites in the IL-23R amplicon. The number in each box represents the size of each exon in nucleotide. The P5/P6 primer set amplifies the IL-23R gene from exon 4 to exon 11. The wild-type IL-23R amplicon contains two EcoRI sites, that when digested, will yield three fragments with the following sizes: 403, 343, and 155 bp. (b) digestion products of the IL-23R. P5/P6 PCR products were digested with EcoRI. The wild-type (Lane 1) yields the digestion pattern: 403, 343 & 155; the pΔ5 (71 nt) (Land 3) gives digestion pattern: 505, 332 & 155 bp and the exon 9a insertion (Lane 4) shows digestion pattern: 343, 332 and 155 bp. (c) schematic of the pre-mRNA containing both the pΔ5 (71 nt) and exon 9a insertion splice events. Shaded area indicates the partial deletion of exon 5. The exon 9a insertion is located in intron 9 that is 5.5 kb downstream of exon 9.

In this series of studies, we prepared total RNA from the peripheral blood mononuclear cells (PBMC) of four healthy adult volunteer donors, stimulated with either 5 μg/ml concanavalin A (ConA), 0.2 μg/ml lipopolysaccharide (LPS), 5 μg/ml phytohaemagglutin (PHA), and 20 ng/ml phorbol myristate acetate (PMA) plus 1 μM ionomycin (P/I). The RNA was reverse transcribed and then the cDNA was subjected to PCR using primers (P5 & P6) as previously described. These primers cover the region between exon 4 to exon 11, which encodes the major part of the human IL-23Rα chain protein (FIG. 4a). Following PCR, products were cloned directly into TOPO-TA pCR2.1 (Invitrogen, Carlsband, Calif.), for further screening and characterization.

The wild-type (i.e., non-variant; e.g., NM_144701) IL-23R P5/P6 fragment contains two EcoRI recognition sites (FIG. 4a). Thus, when EcoRI is used to release the PCR-product insert from the cloning vector, three fragments of the insert are visible: (i) 403 bp (exon 4-7); (ii) 155 bp (exon 7-8); and (iii) 343 bp (exons 8-11; FIG. 4a).

Among the many variants present, one transcript generated from the PMA and ionomycin stimulated PBMC demonstrated a novel digestion pattern that was incompatible with solely exon deletion variation. This transcript yielded fragments of 505 bp, 332 bp, 155 bp, respectively (FIG. 4b) suggesting that more than one possible alternative splicing event might have occurred in the transcript: a deletion within the exon 4-7 region and an insertion in the exon 8-11 region.

Figure 5:
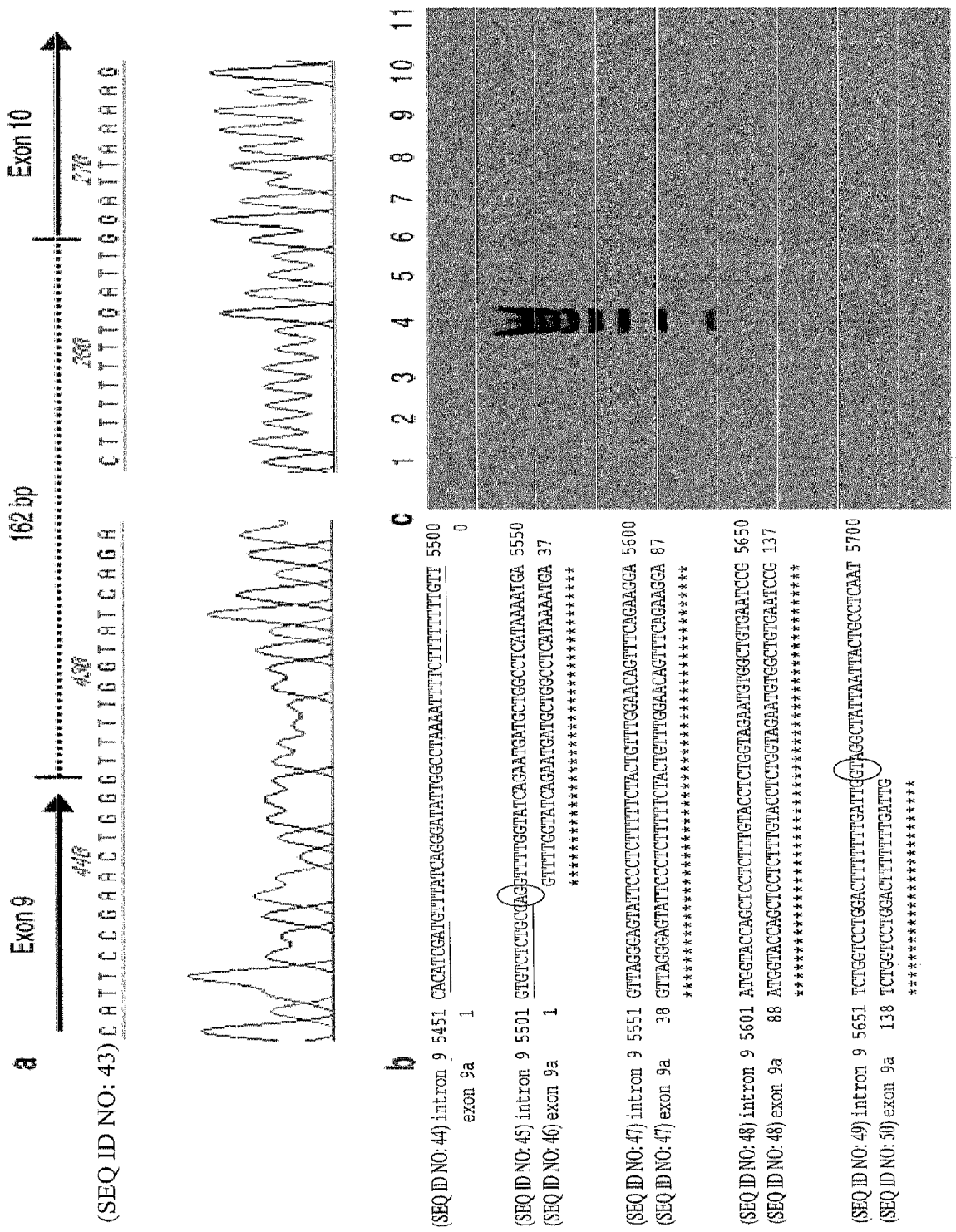
FIG. 5 depicts sequence confirmation and the expression of the exon 9a insertion variant. (a) sequencing analysis was performed to confirm the insertion at exon 9. (b) the upper sequence is the genomic IL-23R sequence within the intron 9 and the lower sequence of cryptic exon 9a. Flanking the insertion, with solid arrowheads above, are the GT/AG donor-acceptor splice sites. Additionally, upstream of the sequence are the putative splice factor binding sites, the polypyrimidine tract (with solid underline) and the branch point sequence ACATCGA (with dashed underline). (c) the results of the nested PCR to detect the existence of exon 9 insertion. Positive control (lane 1), negative control of first PCT (lane 2), water blank (lane 3), DNA ladder (lane 4), empty (lane 5), MegaMan cDNA library (lane 6), PBMC cDNA (lane 7), cDNA from PBMC stimulated with concanavalin A cDNA (lane 8), cDNA from PBMC stimulated with LPS (lane 9), cDNA from PBMC stimulated with PHA/ionomycin (lane 10).

Sequence analysis of the cloned variant IL-23R transcript revealed a compound splicing event had occurred within this amplicon: a previously-observed partial deletion of exon 5 (the first 71 nucleotides), together with a novel 162 nucleotide insertion between exons 9 and 10 (FIG. 4c). The alignment of the insertion against the IL-23R gene showed its location to be within intron 9; 5.5 kb downstream of exon 9. A GT/AG splice donor-acceptor site, required for the pre-mRNA processing, was discovered on both sides of this 162 bp insertion. Additionally, cis-acting sequences (a polypyrimidine tract and a possible branch point sequence (CATCGAT)) are located upstream of the AG splice acceptor site; these are important and conserved in the splicing acceptor area for the correct binding and recognition of splicesome subunits. (FIGS. 5a and 5b). Importantly, these suggest that this 162 bp insertion is likely to be a legitimate cryptic exon when alternative splicing occurs. For nomenclature purposes, we termed this cryptic exon "exon 9a".

Although, this 162 bp exon is likely to be introduced as an in-frame insertion, a TGA stop codon was identified after the translation of 10 amino acids, causing an early termination of the IL-23Rα chain protein. This early termination would result in a truncated intracellular domain of the IL-23Rα. The truncated intracellular domain does not extend to the usual three signaling tyrosine residues in the phosphorylation motif boxes. Similar to the other splice variant, containing a 67 base pairs partial deletion in the exon 11 of the IL-23R, was also found to show a putative intracellular region missing two of the three signaling tyrosine residues. Thus, binding of IL-23 to an IL-23R complex, containing these truncated isoforms, may cease the initiation of the downstream signal transduction. Hence, the 162 bp insertion, causing a truncated IL-23R, suggests a possible non-responsive receptor isoform in the IL-23 signaling.

To determine if the exon 9a insertion is found in previous donors stimulated with various mitogens, a primer set spanning the exon 9+exon 9a and exon 10+exon 9a junctions, were used to amplify the cDNA obtained from all donors with different stimuli. A band of the expected size (162 bp) and of modest intensity was seen in all samples tested, following nested PCR amplification (FIG. 5c). The low expression of exon 9a suggests it is an isoform resulting from a rare alternative splicing of the pre-mRNA.

To understand the possible biological function of this exon 9a insertion within the IL-23R gene, a genome-wide "BLAT" search was carried out to determine if this insertion exists elsewhere in the human genome. The results from this search yielded approximately 200 sequences with more than 90% homology. Interestingly, in most cases these homologous sequences, located on multiple chromosomes (i.e., chromosomes 1, 6, 8, 10, 22, X, etc), also contained the entire set of splicesome binding sites including the AG/GT donor/acceptor sites, polypyrimidine tract and a branch site. These findings suggest this insertional sequence may share similar function throughout the human genome.

Accordingly, a "BLASTx" search was carried out using the 162 bp insertion sequence; the results revealed a 94% identity to a homologous reverse transcriptase human retrotransposon L1 protein (AAB60345). L1 elements are autonomous non-long terminal repeat retrotransposons, i.e., long interspersed nuclear elements (LINE), which have all the necessary machinery needed to insert themselves into random locations throughout the human genome. Moreover, encoded in the insertion sequence are multiple stop codons, in all three reading frames, which suggests that the insertion is acting as a dominant cryptic exon carrying a termination message to halt protein translation. Therefore, in some cases, for example environmental stress, mitogen stimulation, we speculate that the IL-23R may utilize this cryptic exon by alternative splicing to generate a different isoform of the IL-23R producing a shortened intracellular region to cease downstream signaling. Thus, the location in the genome in which the transposon is inserted increases the diversity of the translated protein isoforms.

In conclusion, there is described herein a novel, in frame, insertional variant within the human IL-23R mRNA (exon 9a) between exons 9 and 10. The discovery of these insertions containing high homology throughout the human genome suggests the insertion may include an array of exon information, including splice signaling for pre-mRNA processing, which could act as a transposon shuttling itself within the genome to deliver an early termination message for translation. Additionally, the presence of the exon 9a insertion appears to be present in small amounts in the cDNA of most mitogen stimulated PBMC. This is the first description of an insertional variant of either the α or β domain of the human IL-23R complex.

Example 9

Fragment Analysis of IL-23R Splice Variants in Isolated Immune Cells

We have identified and cloned 24 different IL-23R isoforms. In order to semi-quantitatively measure the mRNA expression level of all the IL-23R isoforms in single PCR reaction, we developed a Fragment Analysis performed on the Beckman CEQ8000 machine.

Figure 6:
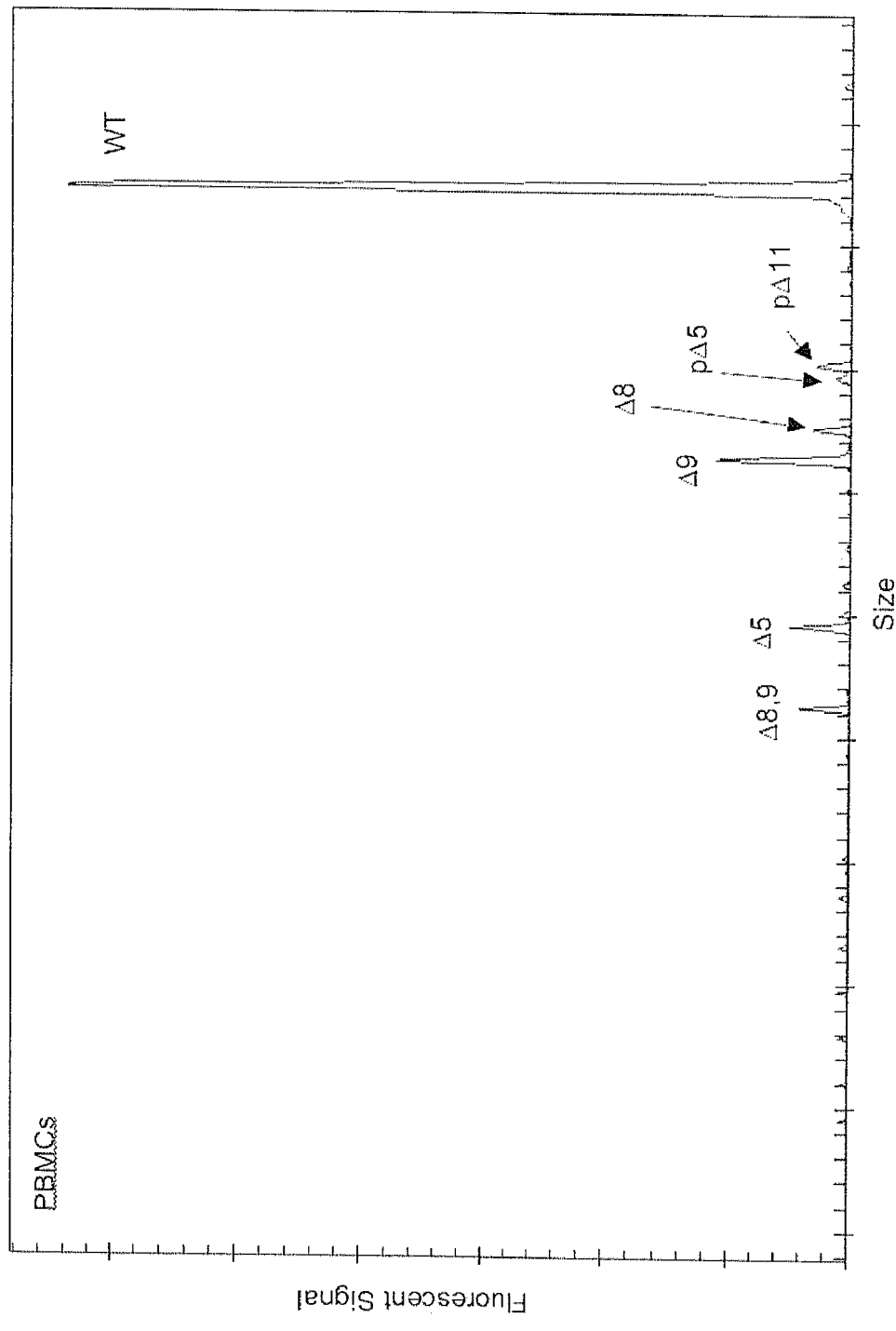
FIG. 6 depicts the expression of IL-23R isoforms in PBMC. The fluorescent signal represents the expression level of specific IL-23R isoforms (e.g., Δ5 and Δ9 etc).

Human PBMC were isolated and used as a cellular model to examine the expression of different IL-23R isoforms. RNA was extracted from the isolated PBMC and its concentration was measured in Nanodrop. Two micrograms of RNA was reversely transcribed into cDNA. A pair of gene specific IL-23R primers (P5 and P6-D3), which one of its was fluorescent labeled (P6-D3), was designed to amplify IL-23R isoforms by PCR. Amplified products were denatured, run on the CEQ8000 machine and separated by size. The fluorescent signal represented the level of expression. We found that PBMC do not express all the IL-23R isoforms, equally, the WT, pΔ11, pΔ5, Δ8, Δ9, Δ5 and Δ8,9 were frequently found (FIG. 6).

We further examined if purified immune cell populations within PBMC can express IL-23R splice variants. B cell, T cell, NK cell and monocyte were purified from PBMC and they were subjected to the Fragment Analysis.

Table 2 summarizes the findings: (i) WT, Δ8, Δ9 and Δ5 were detected in all B cells, T cells, NK cells and monocytes; (ii) pΔ5 was only detected in monocyte; (iii) Δ8,9 was found in T cell, NK cell and monocytes but not in B cells and (iv) Δ5,8, Δ5,6 and Δ5,6,8, were detected in B cells, but not detected in T cells, NK cells and monocytes.

Example 10

Fragment Analysis of IL-23R Splice Variants in Isolated Tissues

In this study, we examined the expression profile of IL-23R isoforms in human tissues. Two micrograms of RNA was reversely transcribed into cDNA. P5/P6-D3 primer pair was used to amplify IL-23R isoforms. The amplified products were analyzed in a CEQ8000 machine.

Figure 7:
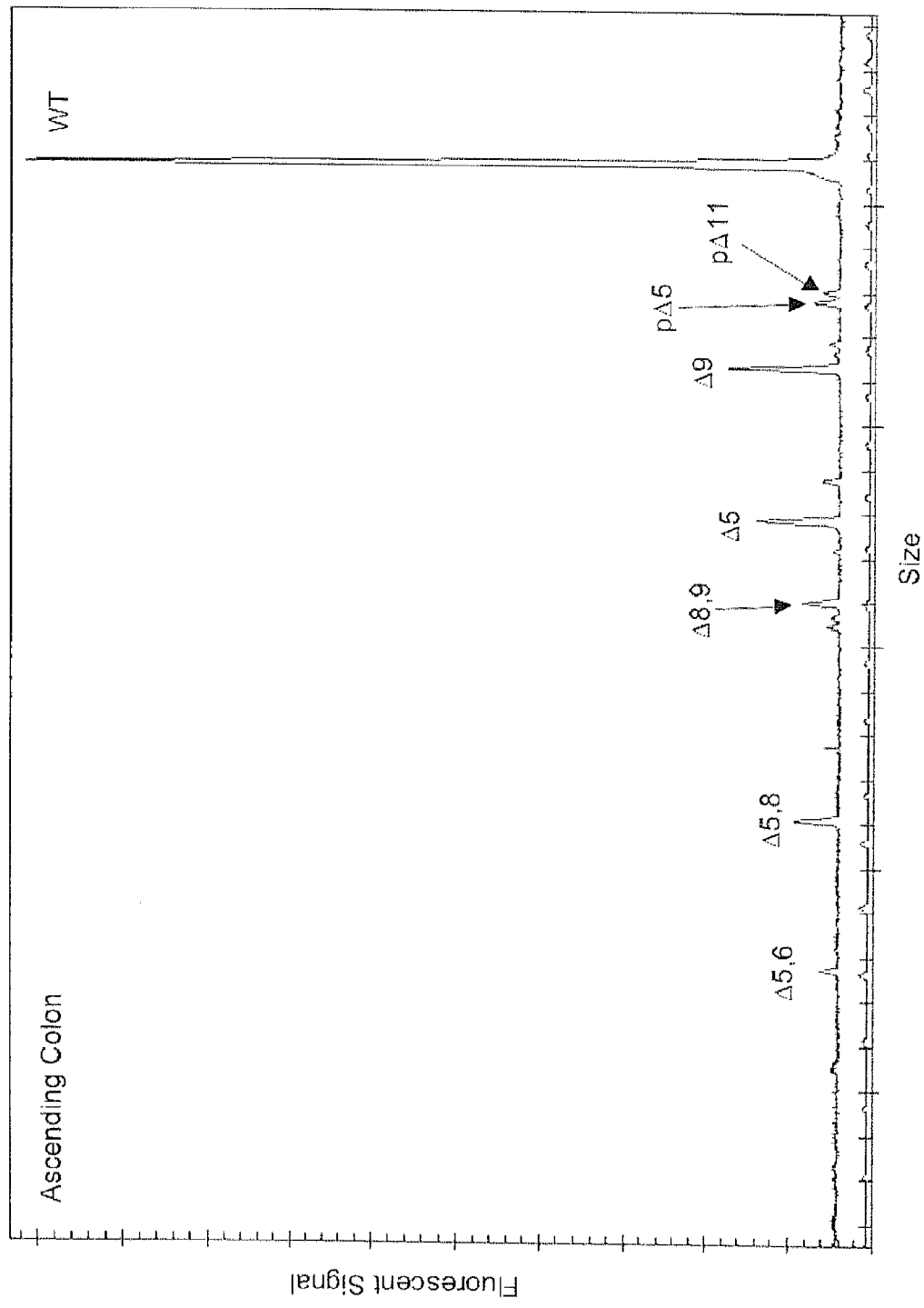
FIG. 7 depicts the expression of IL-23R isoforms in ascending colon in human. The fluorescent signal represents the expression level of specific IL-23R isoforms (e.g., Δ5 and Δ9 etc).
Figure 8:
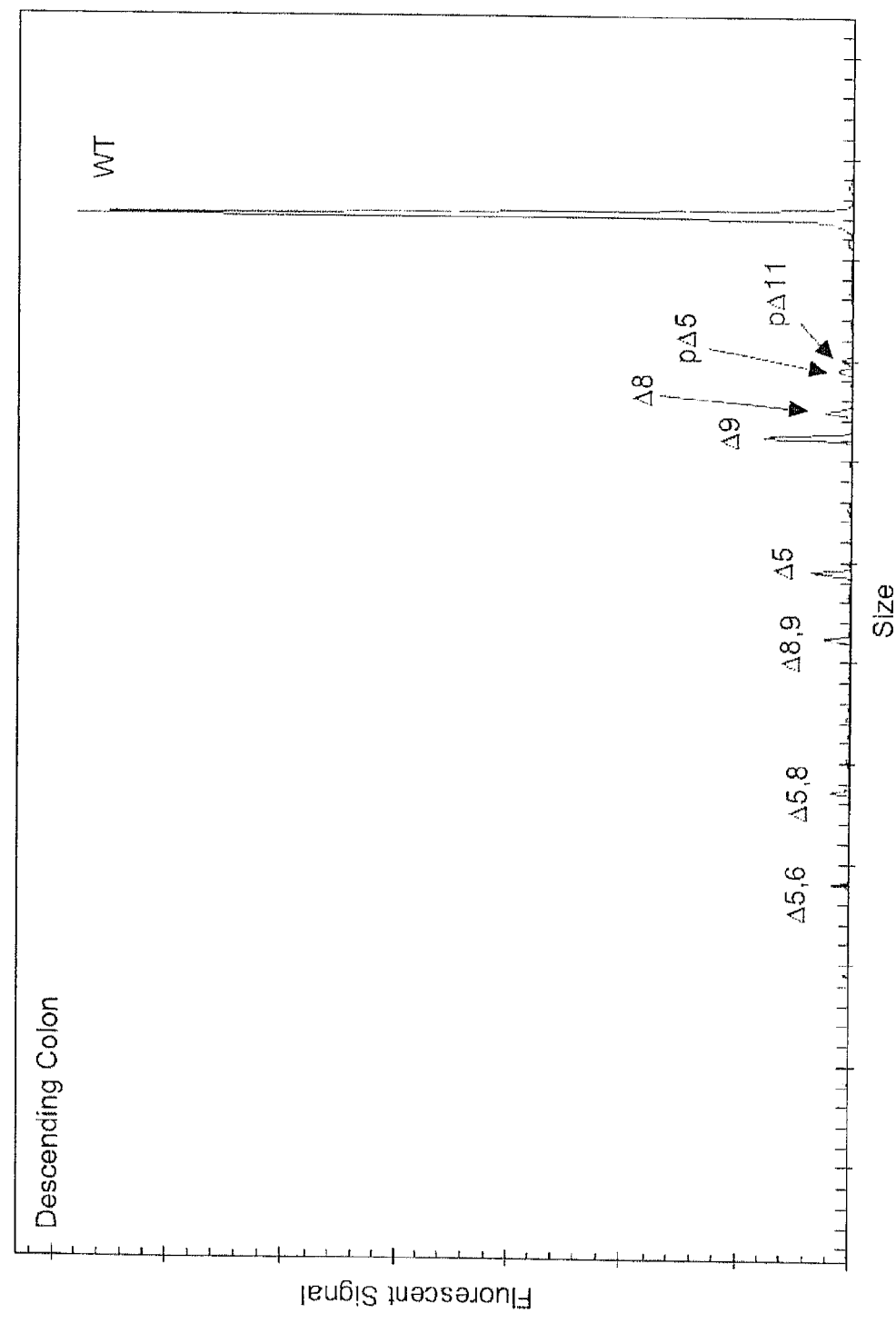
FIG. 8 depicts the expression of IL-23R isoforms in descending colon in human. The fluorescent signal represents the expression level of specific IL-23R isoforms (e.g., Δ5 and Δ9 etc).
Figure 9:
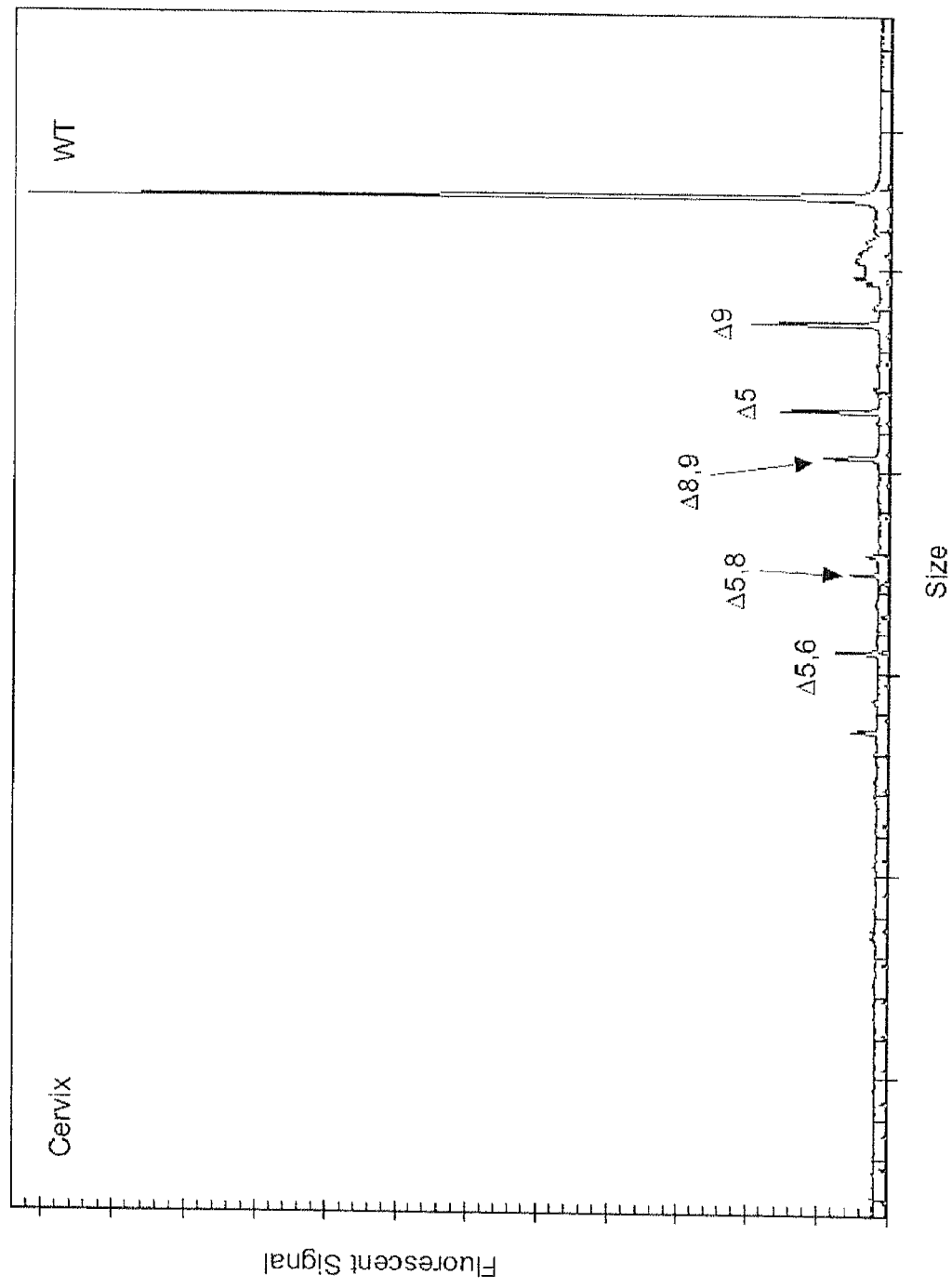
FIG. 9 depicts the expression of IL-23R isoforms in cervix in human. The fluorescent signal represents the expression level of specific IL-23R isoforms (e.g., Δ5 and Δ9 etc).

In both ascending colon tissue (FIG. 7) and descending colon tissue (FIG. 8), we detected nine (9) different IL-23R mRNA transcripts. This includes WT, pΔ11, pΔ5, Δ8, Δ9, Δ5, Δ8,9, Δ5,8 and Δ5,6. In human cervical tissues, we detected six IL-23R isoforms (FIG. 9). This includes WT, Δ9, Δ5, Δ8,9, Δ5,8 and Δ5,6. Table 3 summarizes the expression profile of IL-23R in other human tissues.

Example 11

Development of a Quantitative Assay to Measure Δ9 Isoform

In this study, we developed a Fragment Analysis to examine IL-23R isoform expression. From our study, we found that Δ9 isoform is the major IL-23R isoform among the cells and tissues that we examined. Specifically, we developed an assay using real-time PCR, which can quantitatively measure the expression level of total IL-23R and its Δ9 isoform.

Two pairs of primers were designed: one pair of primers amplified all the reported isoforms to measure the expression level of total IL-23R, and the other pair of primers was Δ9 specific, which only amplify the cDNA of IL-23R isoform when exon 9 was deleted. The Δ9 specific forward primer was designed to span through the junction of exon 8 and exon 10. As such, this forward primer did not anneal to other IL-23R isoforms when exon 9 was presence.

I. PCR Efficiency

Figure 10:
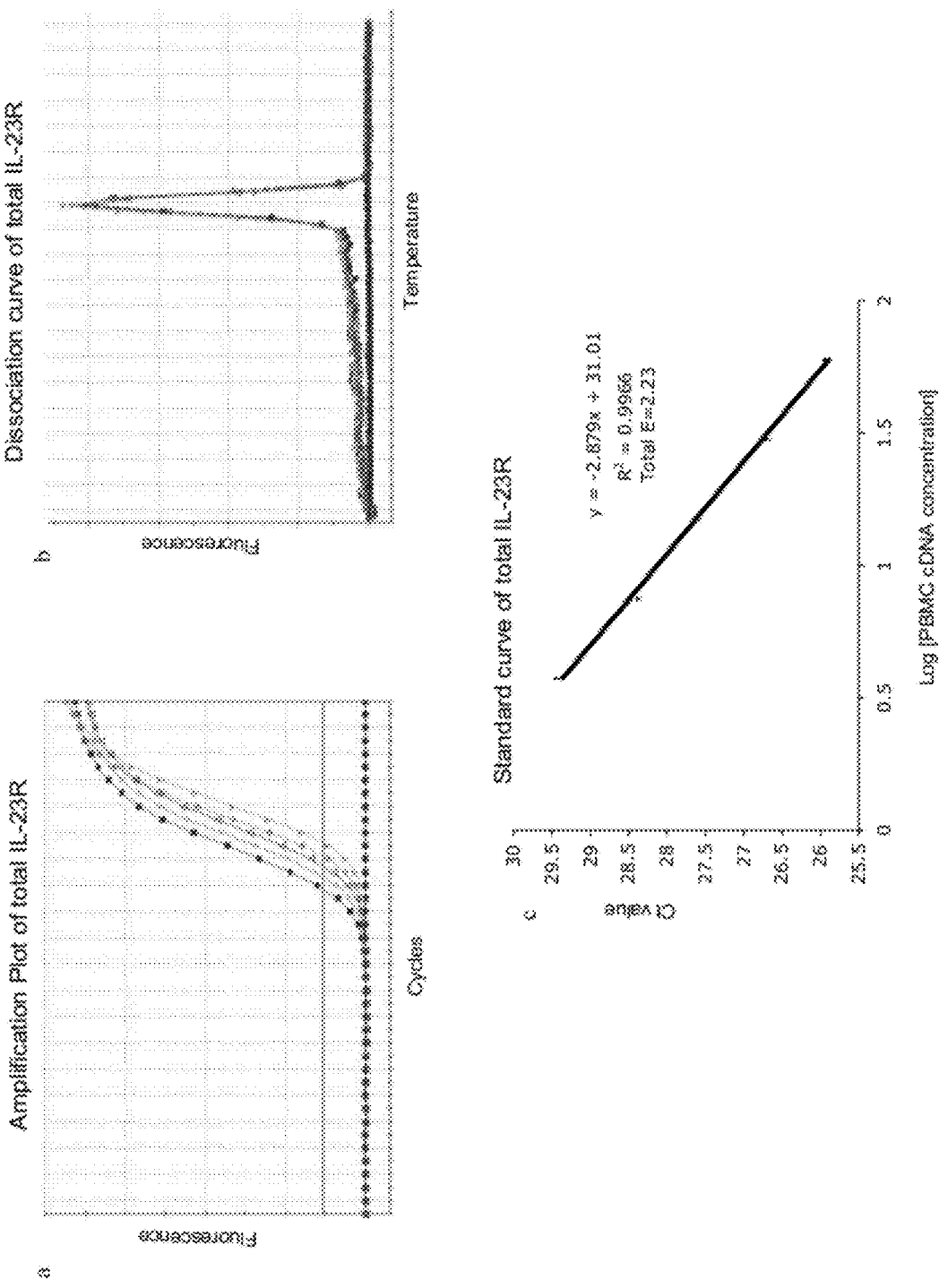
FIG. 10 depicts the quantitative PCR assay for total IL-23R mRNA: (a) amplification plot of total IL-23R in real-time PCR, (b) dissociation curve of total IL-23R, and (c) standard curve of total IL-23R against Ct value. The PCR efficiency (E) is calculated from the slope of the standard curve.

Before using this assay to measure the expression levels of total IL-23R and its Δ9 isoform, a PCR efficiency of these two pairs of primers was measured by a serial dilution (2-fold) of PBMCs cDNA followed by PCR reaction to generate a standard curve. The PCR efficiency value (E) can be calculated by E=10[−1/slope]. Both amplification plots of total IL-23R (FIG. 10a) and its Δ9 isoform (FIG. 11a) showed classical plot indicated that the primer pairs amplified effectively. In addition, single unique peak was found in the dissociation curve concluded that only one PCR product was generated in the real-time PCR (FIGS. 10B (total) and FIG. 11b (Δ9)). Using the equation E=10[−1/slope], the PCR efficiencies of total IL-23R (FIG. 10c) and its Δ9 isoform (FIG. 11c) were 2.23 and 2.0 respectively. Based on this observation, we concluded that both primers are effective in the real-time PCR reaction.

II. Specificity

Figure 12:
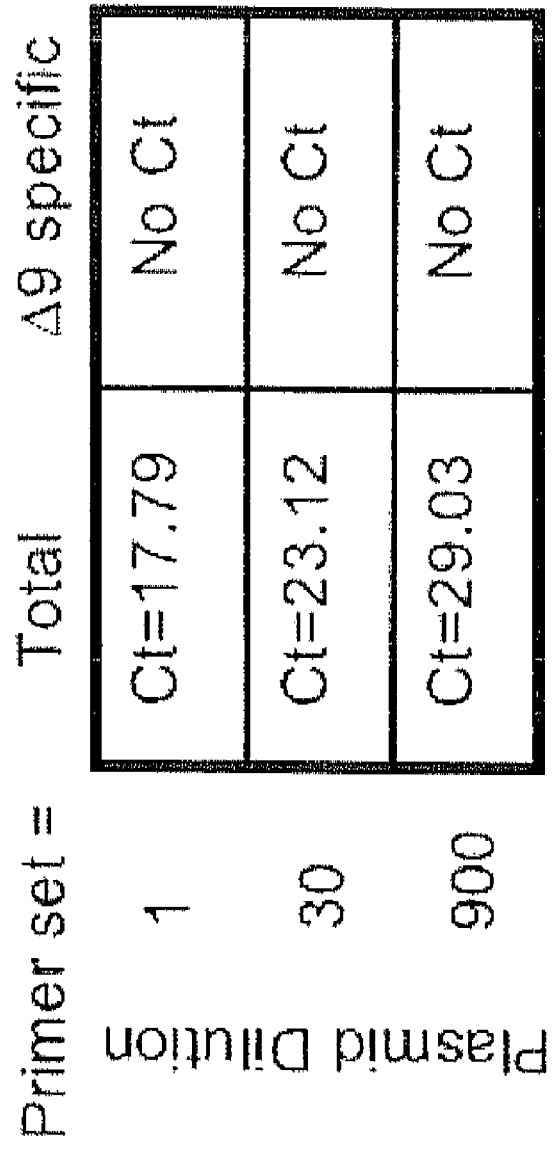
FIG. 12 depicts the specificity of Δ9 specific primer set. Plasmid DNA containing the wild-type IL-23R human cDNA was used as template and diluted by 30 and 900 folds. Real-time q-PCR was performed using either the total IL-23R primer set or the Δ9 specific primer set. No amplification was detected using the Δ9 specific primer set.

In order to confirm the specificity of Δ9 specific primers, DNA plasmid containing the wild-type cDNA was used as template in the real-time PCR reaction. A serial dilution (30 fold) of this plasmid, which covered the physiological level of total IL-23R, was generated. In the real-time PCR, amplification product was only detected in the reaction using total IL-23R primers. However, there was no amplified product detected in the reaction using Δ9 specific primers (FIG. 12). This study confirmed that Δ9 specific primers did not amplify the wild-type IL-23R cDNA. It concluded that other IL-23R isoforms without deletion of exon 9 were not amplified.

Example 12

IL-23R Δ9 Isoform and Colon Tissues in Crohn's Disease

Human IL-23 receptor has been speculated as one of the genetic susceptibility locus in Crohn's disease. In this study, we examined the expression level of Δ9 (ΔCt of Δ9) relative to total IL-23R level in Crohn's disease patients.

I. Patient Subject 1

Figure 13:
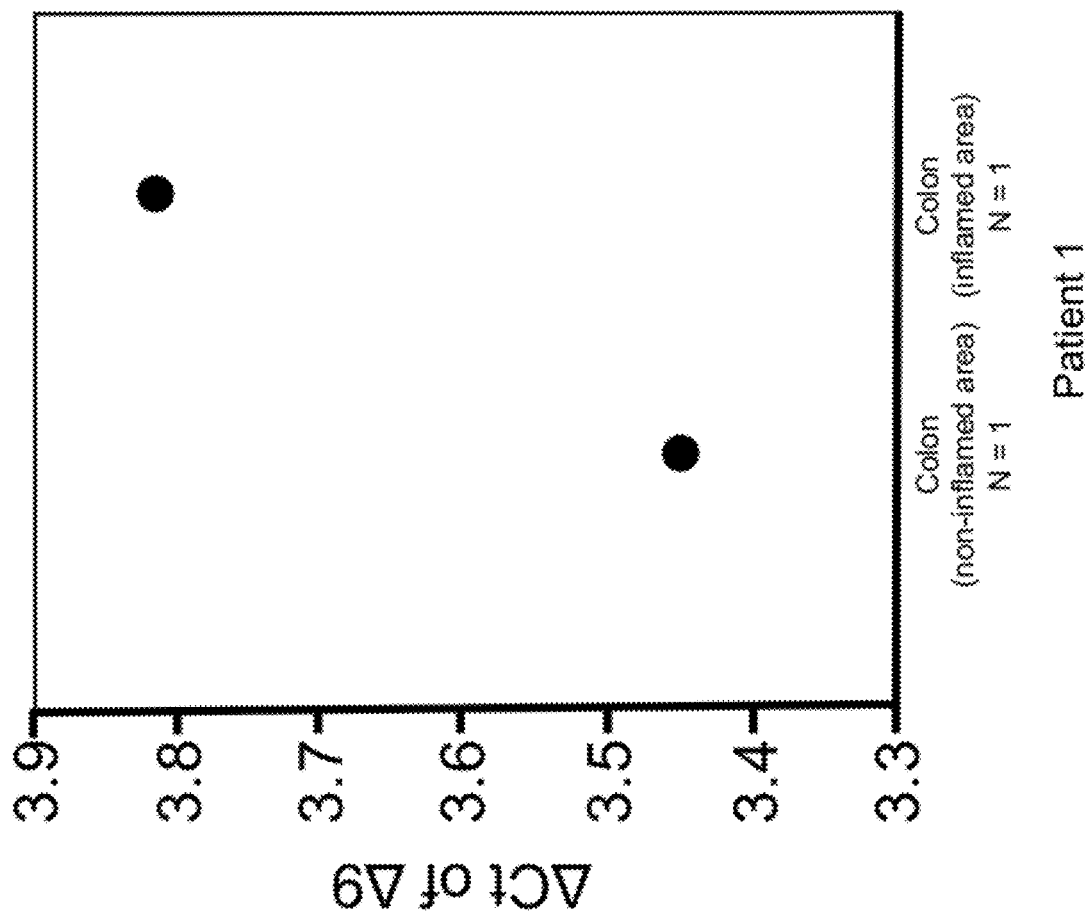
FIG. 13 depicts the relative expression level of Δ9 in non-inflamed areas and inflamed areas of colon from patient #1. The expression level of Δ9 was measured in the colon tissues. The non-inflamed area yielded a higher ΔCt value as compared to that of the inflamed area. Thus, the inflamed area of colon expresses a lower level of Δ9 when compared to that of a non-inflamed area.

First, we prepared a pair-match colon tissue from a patient who had been diagnosed as having active Crohn's Disease. RNA was extracted from colon tissues and reversely transcribed into cDNA. To measure the relative level of Δ9, real-time PCR was performed using total IL-23R primers or Δ9 specific primers. ΔCt of Δ9 was calculated by subtracting Ct value of Δ9 from Ct value of total IL-23R. The higher ΔCt value meant the lower relative expression level of Δ9. ΔCt of Δ9 was 3.44 and 3.87 in the non-inflamed and inflamed areas of colon respectively (FIG. 13).

These results indicate that ΔCt of Δ9 was higher in the colon tissue with inflammation as compared to that without inflammation. This observation further indicates the relative expression level of Δ9 was reduced in the inflamed area of colon tissue from Crohn's disease patient.

Figure 14:
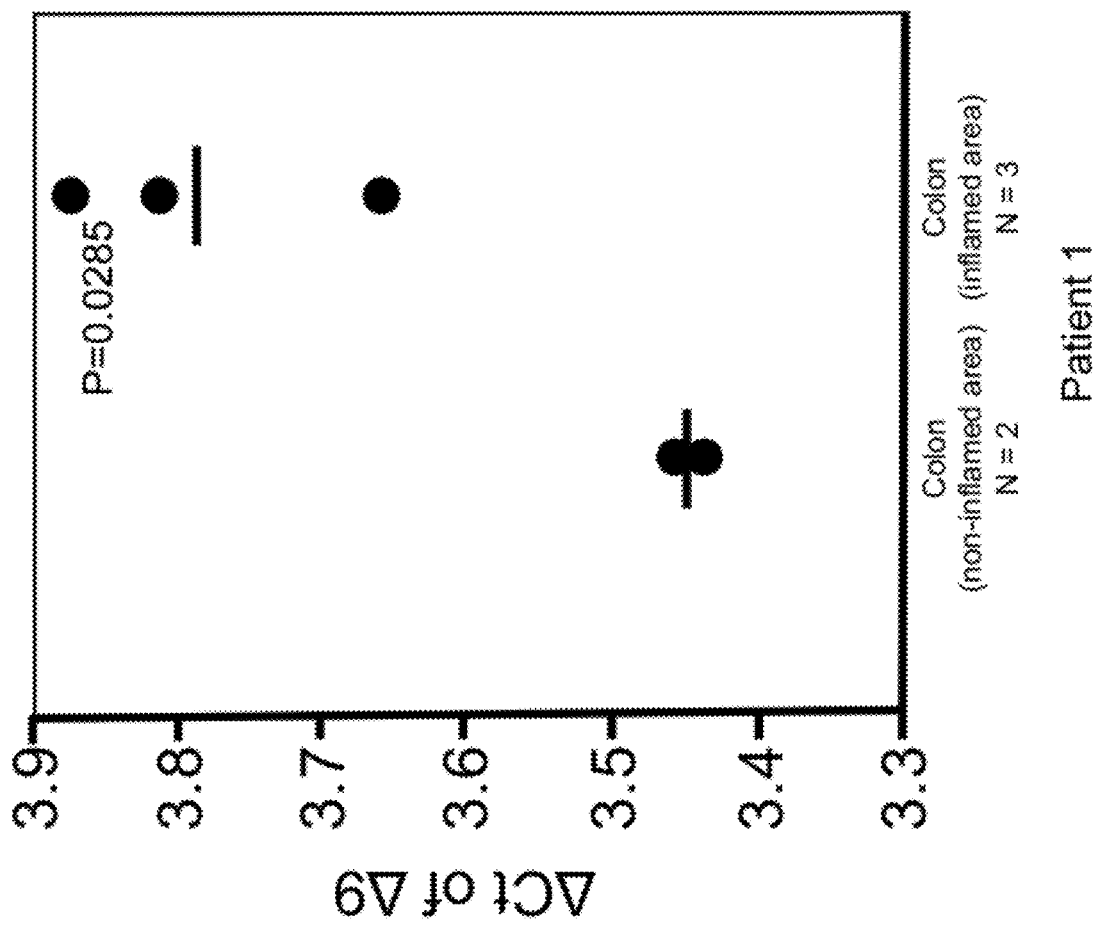
FIG. 14 depicts the relative expression level of Δ9 in non-inflamed areas and inflamed areas of colon from patient #1. Multiple colon tissues were analyzed in this study. Two non-inflamed areas were compared to three inflamed areas. The non-inflamed areas yielded a higher ΔCt value as compared to that of the inflamed areas (i.e., the difference is statistically significance ($P<0.05$)). Thus, the inflamed areas of colon expressed relatively lower level of Δ9 when compared to non-inflamed areas.

We further examined one more non-inflamed area and two inflamed areas from the same patient. We made a similar observation. The difference between the non-inflamed and inflamed area was statistically significance (p<0.05) (FIG. 14).

II. Patient Subjects 2-4

Figure 15:
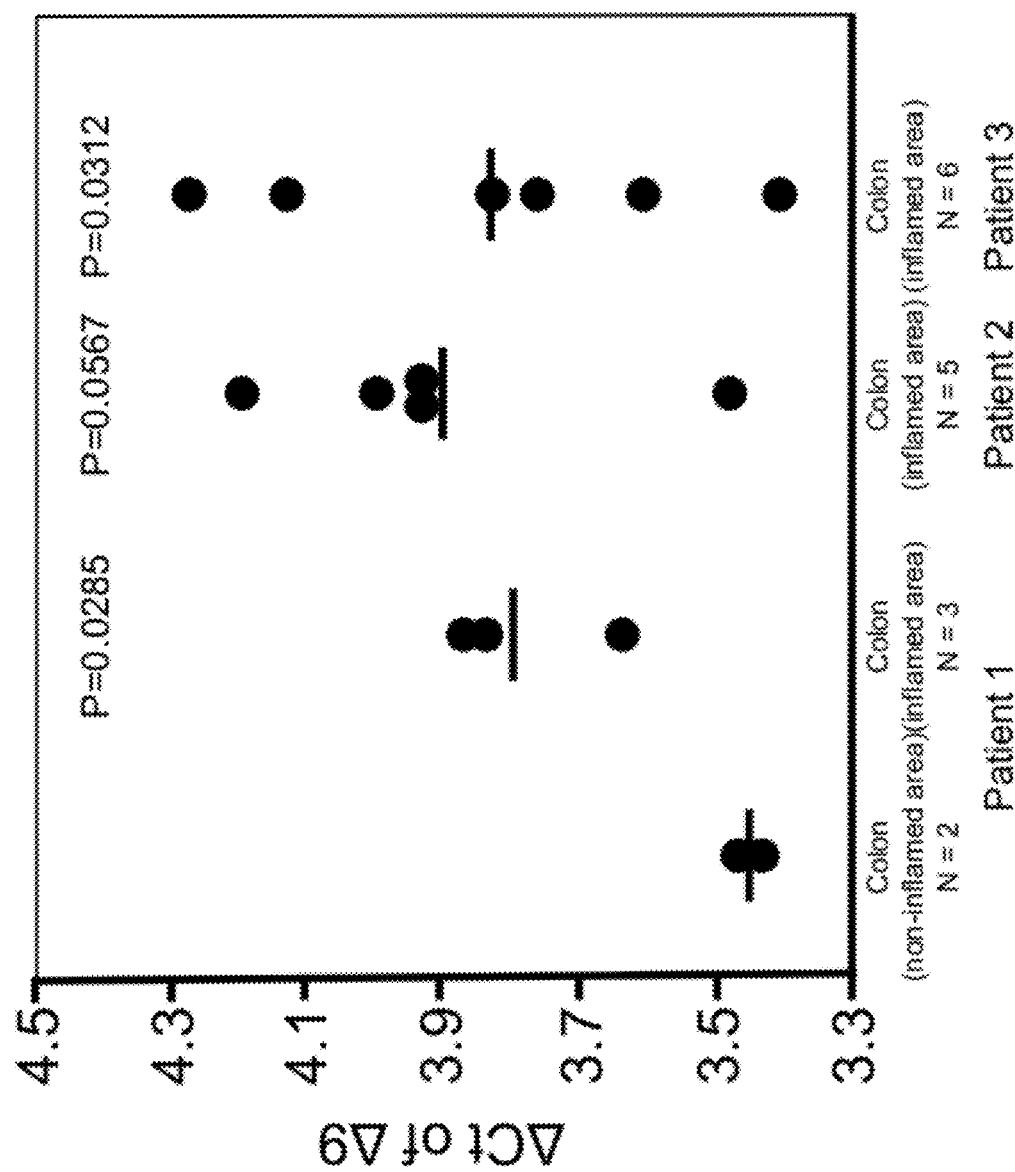
FIG. 15 depicts the comparison of relative expression level of Δ9 in colon tissues from Patient #1, Patient #2 and Patient #3. In Patient #1, the inflamed areas showed a higher ΔCt value as compared to that of non-inflamed areas. In Patient #2, five inflamed areas from colon tissue were analyzed and yielded a higher ΔCt value when compared to the non-inflamed areas of Patient #1. In Patient #3, six inflamed areas from colon tissue were analyzed and yielded a higher ΔCt value as compared to the non-inflamed areas of Patient #1. The differences were statistically significance ($P<0.05$). Both ΔCt values from Patient #2 and #3 were similar to the ΔCt value from Patient #1 inflamed area.

We continued to examine more inflamed areas of colon tissues from two additional Crohn's disease patients (patient #2 and #3). In Patient 2, we analyzed 5 different inflamed areas of colon. The average ΔCt was 3.89. In Patient 3, we analyzed 6 different inflamed areas of colon. The average ΔCt was 3.83. In both patients, the ΔCt values were similar to the inflamed area of colon from Patient #1 (FIG. 15).

Figure 16:
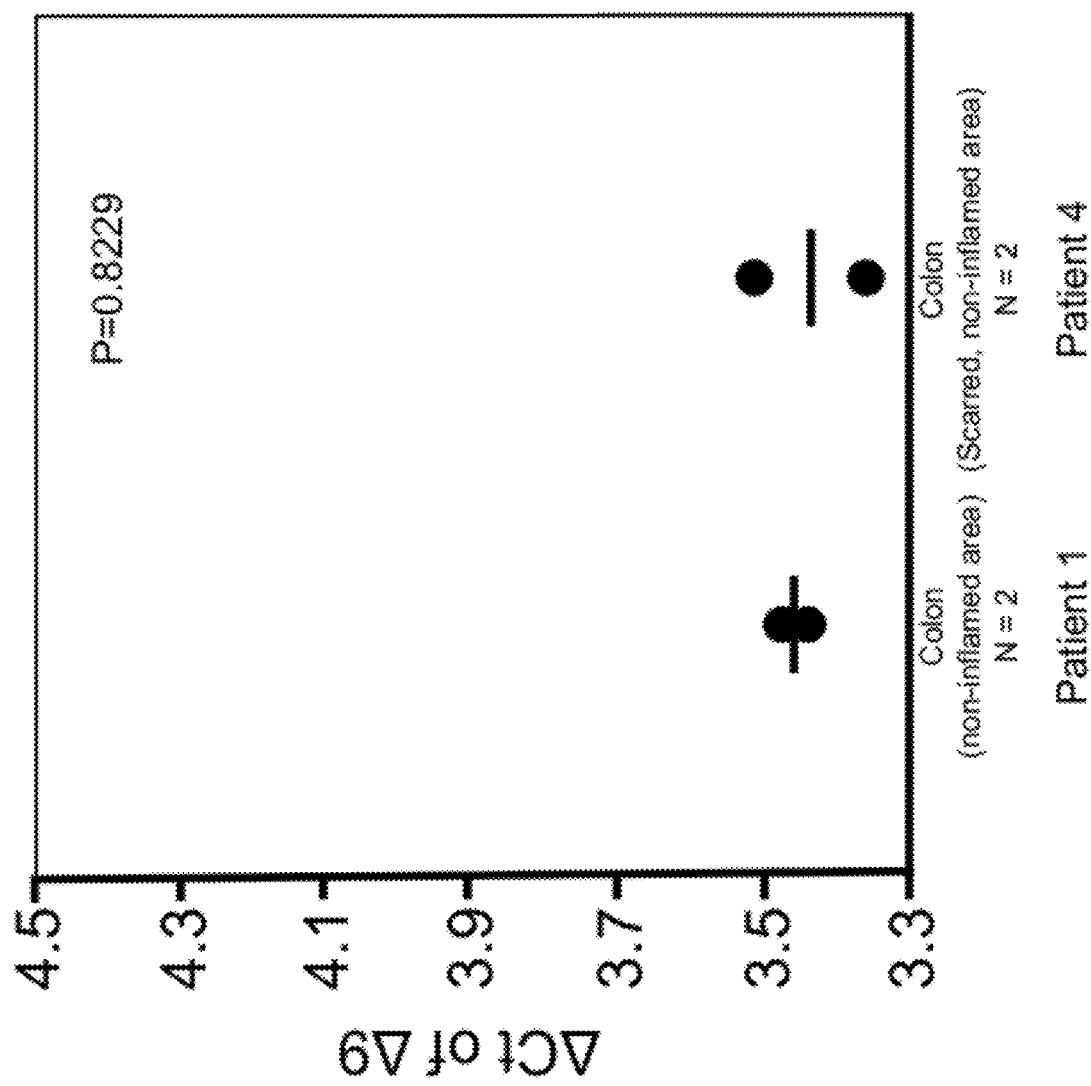
FIG. 16 depicts the comparison of relative expression level of Δ9 in non-inflamed areas of colon tissues of Patient #1 and #4. Two non-inflamed areas from colon tissue in Patent #4 were analyzed and yielded similar ΔCt values when compared to the non-inflamed areas of Patient #1.

In addition to the inflamed areas of colon from different patients, we study non-inflamed (scarred) areas from another active Crohn's disease patient (Patient #4). Two scarred areas without inflammation were examined. The average ΔCt was 3.43, which was similar to the non-inflamed area of colon from Patient #1 (FIG. 16). To summarize our Crohn's disease patient analysis, relative expression level of Δ9 was reduced in the inflamed area compared to the non-inflamed area of colon.

FIG. 17 summarizes the relative level of Δ9 in colon between inflamed tissue area and non-inflamed tissue area. Altogether, these results show the association of ΔCt of Δ9 and inflammation in colon tissue.

Example 10

IL-23R Δ9 Isoform and PBMC in Crohn's Disease

In this study, we sought to develop a diagnostic assay using peripheral blood as a non-invasive approach to detect IL-23R Δ9 isoform in Crohn's patients. Since Δ9 isoform has been showed to express in PBMC and collecting blood represents a non-invasive approach, we used our developed real-time PCR to study the relative expression level of Δ9 in PBMC.

Figure 18:
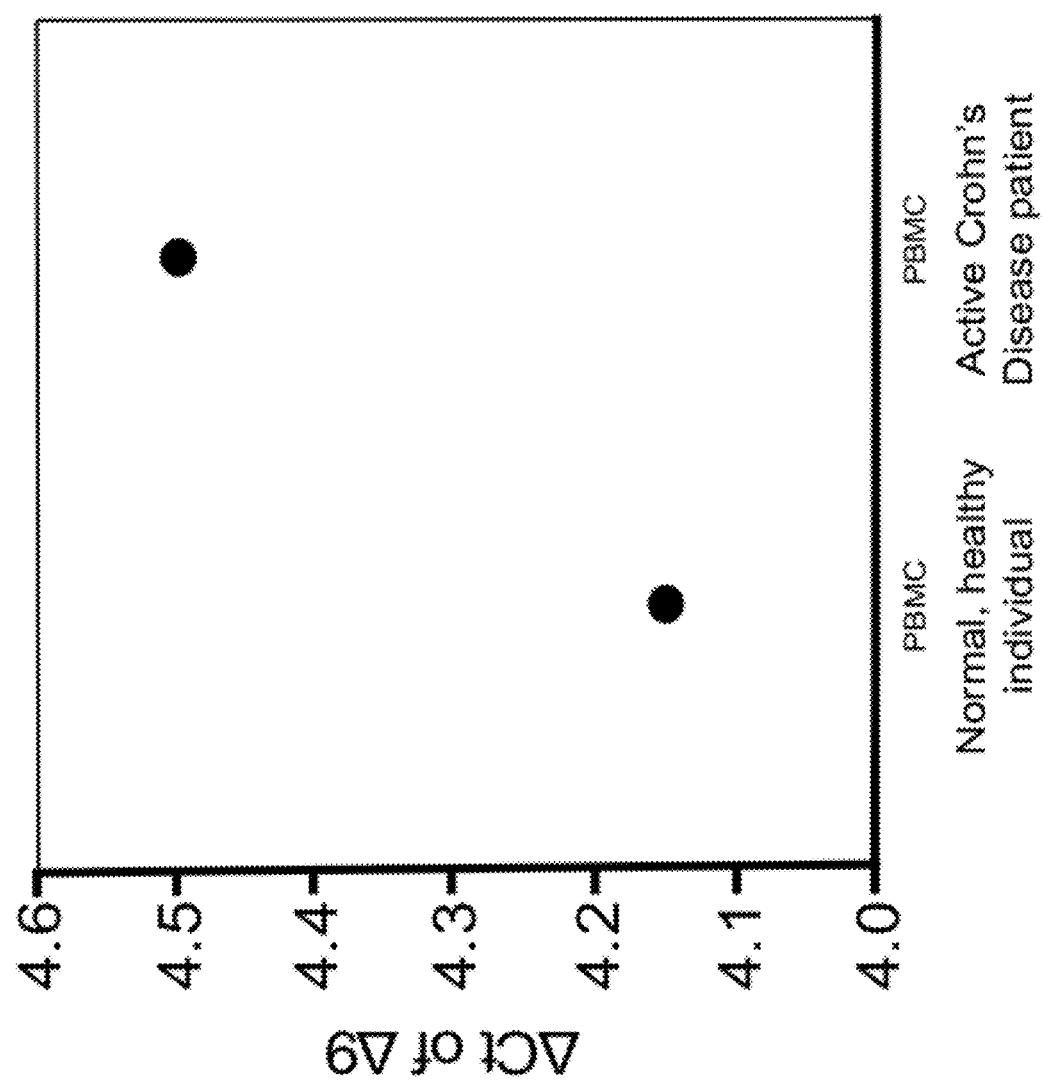
FIG. 18 depicts the relative expression level of Δ9 in PBMC isolated from healthy donor and an active Crohn's disease patient. PBMC isolated from the active Crohn's disease patient yielded a higher ΔCt value when compared to the PBMC isolated from healthy donor, showing lower levels of Δ9.

RNA was extracted from PBMC from healthy donor and active Crohn's disease patient. cDNA was generated and used in the real-time PCR assay. Same calculation method was employed. ΔCt of Δ9 was 4.16 and 4.51 in PBMC from healthy individual and active Crohn's patient respectively (FIG. 18). Consistence with our result in the colon tissue study, PBMC also showed the same observation. The result was summarized in the FIG. 19.

EXPERIMENTAL METHODOLOGY

Purification of Human PBMC and Mitogen Stimulation

Peripheral blood mononuclear cells (PBMC) were isolated from heparinized whole venous blood of healthy donors by density gradient centrifugation using Ficoll-Paque (Sigma) according to the manufacturer's instructions. Isolated PBMC were maintained in RPMI1640 medium (Invitrogen-Gibco) supplemented with 10% heat-inactivated FBS (Invitrogen-Gibco) and 1 mM Glutamine (Invitrogen-Gibco) in the presence of different mitogens (5 μg/ml concanavalin A (ConA), 0.2 μg/ml lipopolysaccharide (LPS), 5 μg/ml phytohaemagglutinin (PHA) and 20 ng/ml phorbol myristate acetate (PMA) plus 1 μM ionomycin (P/I)) for 72 hours at 37° C. in a 5% $CO_2$ humidified atmosphere. These activated PBMC were used for RNA isolation and reverse transcriptase-PCR (RT-PCR).

Nucleic Acid Isolation and Reverse Transcriptase—PCR for cDNA Production

Total RNA was isolated from activated PBMC with the "Absolutely RNA" miniprep kit (Stratagene) following the manufacturer's instructions. Purified RNA (300 ng) was reverse-transcribed with AffinityScript™ cDNA Synthesis Kit (Stratagene) using 300 ng of random hexamer in a volume of 20 μl of reverse transcription mixture. Polymerase chain reaction (PCR) mixture (20 μl) included 1 U "Expand Long Template Enzyme" mix (Roche), 1× buffer and 0.25 μM of each specific primer pairs, with the following thermalcycling parameters: 94° C. for 4 min, 1 cycle; 94° C. for 45 sec, 56° C. for 45 sec, 72° C. for 90 sec, 40 cycles; 72° C. for 10 min, 1 cycle. The primers used to amplify IL-23R gene fragments were as followed:

```
P3:
                                            (SEQ ID NO: 26)
forward primer 5'-GTAGAACCAGCCACAATTTT-3';

P5:
                                            (SEQ ID NO: 27)
forward primer 5'-AATGCTGGGAAGCTCACCTACATA-3';

P6:
                                            (SEQ ID NO: 28)
reverse primer 5'-GCTTGTGTTCTGGGATGAAGATTTC-3'.
```

The primer pairs P3/P6 and P5/P6 generated amplicons sized at 1,234 bp and 901 bp, respectively, from the published sequence (NCBI reference sequence NM_144701). The primer pair P3 and P6 spanned exon 3 to exon 11 and primer pair P5 and P6 spanned exon 4 to exon 11 (FIG. 1a), covering all the possible exon-exon junctions of IL-23R mRNA encoding the mature region of IL-23R wild-type protein.

Cloning and Screening of Splice Variants

Total PCR products from each mitogen stimulation, each from four donors were cloned into the TOPO TA vector (pCR2.1; InVitrogen) and transformed into TOP10 competent cells (InVitrogen). Over 1,500 bacterial colonies were selected and colony PCR was performed using the M13 forward primer and M13 reverse primer. The PCR product (5 μl) was electrophoresed on a 1.5% agarose gel to verify the product size.

Identification and Verification of IL-23R Splice Variants by Restriction Endonuclease Digestion and Sequence Analysis The remaining PCR product was digested overnight at 37° C. with 1 U of EcoRI (Fermentas) in a final volume of 20 μl and 10 μl of the digested products were electrophoresed for 45 min in 2% agarose gel at 150V in TRIS-borate/EDTA buffer. Sequence analyses were further performed on those clones showing abnormal digestion patterns than wild-type IL-23R P5P6-fragment digestion patterns (FIG. 1b) with CEQ™ DTCS kit on the CEQ™ 8000 Genetic Analysis System (Beckman Coulter). DNA sequences were analyzed and aligned with MacVector 9.5.2 (Macvector).

Qualitative Analysis of Human Interleukin-23 Receptor (IL-23R) Isoforms

To qualitatively analyze expression of human IL-23R isoforms, RNA was extracted from cells and subsequently reverse transcribed into cDNA. The cDNA was amplified by IL-23R gene specific primer P5 and P6. The amplified product was then analyzed in Beckman CEQ8000. The detailed procedures for each step were described as follows:

RNA Extraction from PBMC and Purified Immune Cells

RNA extraction was performed by using Absolutely RNA Miniprep Kit from Stratagene (400800). Human PBMC was firstly centrifuged at 1000×g for 5 minutes. The supernatant was aspirated and the cell pellet was re-suspended in 300 μl of lysis buffer with the addition of 2 μl of β-mercaptaehanol (14.2 M) by vortexing. Homogenate was transferred to a prefilter spin cup and spun for 5 minutes at 13.3K RPM. 300 μl of 70% ethanol was added to the filtrate followed by vortexing for 5 seconds to mix thoroughly. The mixture was transferred to an RNA binding spin cup and spun for 1 minute at 13.3K RPM. The filtrate was discarded. The RNA binding spin cup was washed with 600 μl low-salt wash buffer. 50 μl DNase solution was directly added onto the fiber matrix inside the spin cup and incubated at 37° C. for 15 minutes in an air incubator. 600 μl if high-salt wash buffer following by 600 μl of low-salt wash buffer was used to wash the spin cup.

30 μl of elution buffer was added directly onto the center of the fiber matrix inside the spin cup and the tube was incubated at room temperature for 2 minutes. The tube was spun at 13.3K RPM for 1 minute to elute the RNA. The concentration of purified RNA was measured by NanoDrop (Thermo Scientific) and stored at −80° C.

Tissue RNA

Tissue RNA was purchased from Stratagene. Total RNA of human colon, liver, stomach, rectum, cervix, ascending colon, descending colon and duodenum were used to generate cDNA. Tissue cDNA was amplified by P5/P6-D3 primers. The amplified products were subjected to Fragment Analysis.

cDNA Synthesis cDNA synthesis was performed by using AffinityScript QPCR cDNA Synthesis Kit from Stratagene (600559). 10 μl of first strand master mix was mixed with 3 μl of oligo(dT) primer (0.1 μg/μl) and 1 μl of Affinity Script RT/RNase Block enzyme mixture. 2 μg or maximum 6 μl of RNA was added to the mixture. The total volume was brought to 20 μg by adding RNase-free $H_2O$. The reaction was incubated at 25° C. for 5 minutes to allow primer annealing following by 42° C. for 45 minutes to allow cDNA synthesis. To maximize the synthesis, the reaction was then incubated at 55° C. for additional 45 minutes. The cDNA synthesis reaction was terminated by incubating the reaction at 95° C. for 5 minutes. The reaction was carried out at the Biometra T-Gradient PCR machine. The completed cDNA synthesis was diluted with dd H2O to 50 μl and placed at −20° C.

PCR Amplification

In order to amplify the human IL-23R isoforms, gene specific primers were designed according to the NCBI GenBank database. The accession number for human IL-23R was NM_144701. P5 (5' AATGCTGGGAAGCTCACCTACATA 3') (SEQ ID NO:27) forward primer and P6 (5' D3-GCTTGTGTTCTGGGATGAAGATTTC 3') (SEQ ID NO:28) reverse primer, which was fluorescently labeled with D3, primers were synthesized by Integrated DNA Technologies. 6% of cDNA (30 was amplified by 0.25 μM of P5/P6-D3 primers using Expand Long Template PCR system from Roche (11681834) for 40 cycles at the Biometra T-Gradient PCR machine. The PCR reaction was carried out at 20 μl volume. The PCR program was as following:

Step 1: 95° C. for 3 minutes (Denaturation)
Step 2: 95° C. for 30 seconds (Denaturation)
Step 3: 60° C. for 45 seconds (Annealing)
Step 4: 68° C. for 2 minutes (Extension)
Step 5: Repeat step 2 to 4 for 34 cycles
Step 6: 68° C. for 10 minutes Analysis of Amplified PCR Products (Fragment Analysis)

Analysis of amplified products was performed by using Fragment Analysis Program in the Beckman CEQ8000. Two DNA standard size markers, DNA size standard marker kit 600 (Beckman 608095) and custom made D1 labeled 600-1200 size marker (Bioventures, Inc) were used in 1:2 ratio respectively to cover the DNA size from 60 to 1200 nucleotides. 10% (2 μl) of amplified products and 1.5 μl DNA size standard were denatured in 36.5 μl GenomeLab Sample Loading Solution (Beckman 608082). After the denaturation, the amplified products and DNA size standard were run through the capillary. The D3 fluorescent signal was directly proportional to the level of P5/P6-D3 amplified products. The size of products was calculated based on the D1-labeled DNA size standard.

Quantitative Measurement of Human Total IL-23R and its Δ9 Isoform Levels in Crohn's Disease Patient The RNA prepared from colon tissues of Crohn's disease patient was reverse transcribed into cDNA. Quantitative measurement of total IL-23R and its Δ9 isoform levels was performed on Stratagene MX300P real-time PCR machine.

PCR Primer Design, Their Specificities and PCR Efficiencies

Total level of IL-23R was measured by IL-23R RT F1 (5' CATGACTTGCACCTGGAATG 3') (SEQ ID NO:29) and R1 (5'GCTTGGACCCAAACCAAGTA 3') (SEQ ID NO:30). The level of Δ9 isoform was measured by Δ9 F (5' GGCACCTTACTTCTGGATTAAAAG 3') (SEQ ID NO:31), which was spanning through the junction of exon 8 and 10, and Δ9 R (5' GGACCTGCTCACTGGAATTA 3') (SEQ ID NO:32).

In order to measure the specificity of Δ9 primers, a serial dilution of plasmid construct containing wild-type IL-23R cDNA was used as a template. PCR efficiencies (E) for different primer sets were also measured by using PBMCs cDNA to generate standard curve. The E values were calculated from the slope of standard curve by the following equation:

PCR efficiency $E = 10^{[-1/\text{slope}]}$

RNA Extraction from Clinical Samples

Biopsy samples of colon tissue were stored in RNAlater (Ambion) at 4° C. to preserve the RNA. RNA extraction was performed by using Absolutely RNA Miniprep Kit from Stratagene (400800). Colon tissue was transferred from the RNAlater to 300 µl of lysis buffer with the addition of 2 µl of β-mercaptaehanol (14.2 M). Tissue was homogenized by Pestle Grinder (Fisher Scientific 03-392-106) in the lysis buffer. Homogenate was transferred to a prefilter spin cup and spun for 5 minutes at 13.3K RPM. 300 µl of 70% ethanol was added to the filtrate followed by vortexing for 5 seconds to mix thoroughly. The mixture was transferred to an RNA binding spin cup and spun for 1 minute at 13.3K RPM. The filtrate was discarded. The RNA binding spin cup was washed with 600 µl low-salt wash buffer. 50 µl DNase solution was directly added onto the fiber matrix inside the spin cup and incubated at 37° C. for 15 minutes in an air incubator. 600 µl if high-salt wash buffer following by 600 µl of low-salt wash buffer was used to wash the spin cup. 30 µl of elution buffer was added directly onto the center of the fiber matrix inside the spin cup and the tube was incubated at room temperature for 2 minutes. The tube was spun at 13.3K RPM for 1 minute to elute the RNA. The concentration of purified RNA was measured by NanoDrop (Thermo Scientific) and stored at −80° C.

Real-Time PCR

Real-time PCR was performed by using Brilliant II SYBR Green QPCR Master Mix (Stratagene 600828). 4 µl (8%) of cDNA was mixed with QPCR reaction mix containing reference dye (ROX). PCR was performed in 20 µl reaction volume using the following condition. Each sample was done in triplicate.

Step 1: 95° C. for 10 minutes (Denaturation)
Step 2: 95° C. for 30 seconds (Denaturation)
Step 3: 60° C. for 30 seconds (Annealing)
Step 4: 72° C. for 1 minute (Extension)
Step 5: Repeat step 2 to 4 for 39 cycles (Amplification)
Step 6: 95° C. for 1 minute
Step 6: 55° C. for 30 seconds (Generation of dissociation curve)
Step 6: 95° C. for 30 seconds Data Analysis The SYBR Green fluorescent signal represented the amount of amplified products was normalized with a passive reference dye (ROX) to compensate for non-PCR related variations in fluorescence. The relative expression level of Δ9 (ΔCt) was calculated by subtracting the average Ct value of Δ9 from the average Ct value of total IL-23R. The ΔCt value of Δ9 was plotted in a dot plot. The average ΔCt value and p-value were calculated.

The Examples are merely illustrative of the invention and are not intended to limit the scope of the invention. One of skill in the art will recognize that various modifications may be made to the embodiments described herein without departing from the spirit and scope of the invention, which is defined by the appended claims. All references cited herein, including patents, journals, and GenBank accession nos., are incorporated by reference in their entirety.

References

1. Association scan of 14,500 nonsynonymous SNPs in four diseases identifies autoimmunity variants. (2007) Nat. Genet. 39(11):1329-37 2. Baker K E and Parker R. Nonsense-mediated mRNA decay: terminating erroreous gene expression. (2006) Curr Opin Cell Biol 16:293-99.
3. Begovich A B, Chang M, Caillier S J, Lew D, Catanese J J, Wang J, Hauser S L, Oksenberg J R. The autoimmune disease-associated IL12B and IL23R polymorphisms in multiple sclerosis. (2007). Hum Immunol. 68(11):934-7.
4. Black D L. Mechanisms of alternative pre-messenger RNA splicing. (2003). Annu Rev. Biochem. 72: 291-336.
5. Capon F, Di Meglio P, Szaub J, Prescott N J, Dunster C, Baumber L, Timms K, Cutin A, Abkevic V, Burden A D, Lanchbury J, Barler J N, Trembath R C, Mestle F O. (2007) Sequence variants in the genes for the interleukin-23 receptor (IL23R) and its ligand IL12B confer protection against psoriasis. Hum Genet. 121: 201-6.
6. Duerr, RH, Taylor, K D, Brant, S R et al. A genome-wide association study identifies IL23R as an inflammatory bowel disease gene. (2006) *Science* 314: 1461-1463.
7. Graveley, BR. (2001) Alternative splicing: increasing diversity in the proteomic world. Trends Genet. 17:100-107.
8. Illes Z, Safrany E, Peterfalvi A, Magyari L, Farago B, Pozsonyi E, Rozsa C, Komoly S, Melegh B. 3'UTR C2370A allele of the IL-23 receptor gene is associated with relapsing-remitting multiple sclerosis. (2008) Neurosci Lett. 24; 431(1):36-8.
9. Langrish C L, McKenzie B S, Wilson N J, de Waal Malefyt R, Kastelein R A, Cua D J. IL-12 and IL-23: master regulators of innate and adaptive immunity. Immunol Rev 2004 202: 96-105.
10. Levine S J (2004) Mechanisms of soluble cytokine receptor generation. J. Immuno. 173:5343-8.
11. Lewis B P, Green R E, and Brenner S E. Evidence for the widespread coupling of alternative splicing and nonsense-mediated mRNA decay in humans. (2003) PNAS 100: 189-92.
12. Maquat L E. (2004) Nonsense-mediated mRNA decay: Splicing, translation and mRNP dynamics. Nat Rev Mole Cell Biol. 5: 89-99.
13. Nair R P, Ruether A, Stuart P E, Jenisch S, Tejasvi T, Hiremagalore R, Schreiber S, Kabelitz D, Lim H W, Voorhees J J, Christophers E, Elder J T, Weichenthal M. (2008) Polymorphisms of the IL12B and IL23R Genes Are Associated with Psoriasis. (2008) J Invest Dermatol.
14. Parham, C, Chirica, M, Timans, J et al. A receptor for the heterodimeric cytokine IL-23 is composed of IL-12R-beta-1 and a novel cytokine receptor subunit, IL-23R. (2002) *J. Immun.* 168: 5699-5708.
15. Raelson J V, Little R D, Ruether A, Fournier H, Paquin B, Van Eerdewegh P, Bradley W E, Croteau P, Nguyen-Huu Q, Segal J, Debrus S, Allard R, Rosenstiel P, Franke A, Jacobs G, Nikolaus S, Vidal J M, Szego P, Laplante N, Clark H F, Paulussen R J, Hooper J W, Keith T P, Belouchi A, Schreiber S. (2007) Genome-wide association study for Crohn's disease in the Quebec Founder Population identifies multiple validated disease loci. Proc Natl Acad Sci USA. 11; 104(37):14747-52.

16. Roos I M, Kockum I, Hillert J. The interleukin 23 receptor gene in multiple sclerosis: A case-control study. (2007) J. Neuroimmunol.
17. Rueda B, Orozco G, Raya E, Fernandez-Sueiro J L, Mulero J, Blanco F J, Vilches C, González-Gay M A, Martin J. The IL23R Arg381Gln non-synonymous polymorphism confers susceptibility to ankylosing spondylitis. (2008) Ann Rheum Dis.
18. Sartor R B. Mechanisms of diseases: pathogenesis of Crohn's diseases and ulcerative colitis. Nat Clin Pract Gasteroenterol Hepatol 3: 390-407 (2006)
19. Van de Vosse E, Lichtenauer-Kaligis E, van Dissel J T, Ottenhoff T H M (2003). Genetic variations in the interleukin-12/interleukin-23 receptor (β1) chain, and implications for Il-12 and Il-23 receptor structure and function. Immunogenetics 54:817-829.
20. Weaver C T, Hatton R D, Mangan P R, Harrington L E. (2007) IL-17 family cytokines and the expanding diversity of effector T Cell Lineages Annu Rev Immunol 25:821-52.
21. Yang X O, Panopoulos A D, Nurieva R, Chang S H, Wang D, Watowich S S, Dong C. STAT3 Regulates Cytokine-mediated Generation of Inflammatory Helper T Cells (2007) JBC 282: 9358-63.
22. Zhang, XY, Zhang, HJ, Zhang, Y, et al. Identification and expression analysis of alternatively spliced isoforms of human interleukin-23 receptor gene in normal lymphoid cells and selected tumor cells. (2006) *Immunogenetics*. 57: 934-943.
23. Oppmann B, Lesley R, Blom B, Timans J C, Xu Y, Hunte B, Vega F, Yu N, Wang J, Singh K, Zonin F, Vaisberg E, Churakova T, Liu M, Gorman D, Wagner J, Zurawski S, Liu Y, Abrams J S, Moore K W, Rennick D, de Waal-Malefyt R, Hannum C, Bazan J F, Kastelein R A (2003) Novel p19 protein engages IL-12p40 to form a cytokine, IL-23, with biological activities similar as well as distinct from IL-12. Immunity. 13:715-25.

TABLE 1

Splice code usages of the partial exon skipping in IL23R mRNA

| Transcripts | Splice donor site | Splice acceptor sites | Deletion caused by alternative splicing |
|---|---|---|---|
| pΔ5 5nt | TGTGAAGAGgtagg (SEQ ID NO: 33) | tttgttttaagtttagAGACAGAA (SEQ ID NO: 34) | 5 bp |
| pΔ5 71nt | TGTGAAGAGgtagg (SEQ ID NO: 33) | tttgttttaagtttagAGACAGAA (SEQ ID NO: 34) | 5 bp |
| pΔ11 67nt | ATGCTACAGgtaaccta (SEQ ID NO: 35) | gatccatgattacagAGATAAAGAAA (SEQ ID NO: 36) | 67 bp |
| pΔ5,6,7 | CTGATTCATtacaaggtgg (SEQ ID NO: 37) | cactgtgttttttcatAAAACACCTGAAAC (SEQ ID NO: 38) | 383 bp |
| pΔ5,6,7 | TGGCAAGAAgtacttggtttgggtc (SEQ ID NO: 39) | tggagccaaacattaaGTACGTATTTCA (SEQ ID NO: 40) | 288 bp |
| pΔ7,8 | AAACATTAAgtacgtatttcaag (SEQ ID NO: 41) | gcttccatctctacagGGCACCTTACTTC (SEQ ID NO: 42) | 164 bp |

The possible splice acceptor/donor sites are boxed. The mRNA are in uppercases, and the intron are in lowercase.
The deleted exons compared to the wild-type transcripts are in bold.
The possible polypyrimidine tracts are underlined.

TABLE 2

Expression of IL-23R isoforms in PBMCs and immune cells

| | PBMCs | B cell | T cell | NK cell | Monocyte |
|---|---|---|---|---|---|
| WT | 68.8% | 52.7% | 60.5% | 60.8% | 61.0% |
| pΔ11 | 3.2% | 0.0% | 0.0% | 0.0% | 0.0% |
| pΔ5 | 1.6% | 0.0% | 0.0% | 0.0% | 3.7% |
| Δ8 | 3.8% | 6.1% | 6.0% | 2.2% | 3.2% |
| Δ9 | 12.1% | 18.3% | 16.5% | 19.8% | 18.8% |
| Δ5 | 5.8% | 6.1% | 5.5% | 8.4% | 5.5% |
| Δ8, 9 | 4.7% | 0.0% | 11.5% | 8.8% | 7.8% |
| Δ5, 8 | 0.0% | 5.3% | 0.0% | 0.0% | 0.0% |
| Δ5, 6 | 0.0% | 4.2% | 0.0% | 0.0% | 0.0% |
| Δ5, 6, 8 | 0.0% | 7.1% | 0.0% | 0.0% | 0.0% |

TABLE 3

Expression of IL-23R isoforms in human tissues

| | Duodenum | Ascending Colon | Descending Colon | Colon | Rectum | Cervix |
|---|---|---|---|---|---|---|
| WT | 70.5% | 58.6% | 66.5% | 76% | 64.8% | 67% |
| pΔ11 | 0.0% | 3.8% | 0.0% | 1.1% | 0.0% | 0.0% |
| pΔ5 | 1.6% | 4.2% | 0.0% | 1.2% | 3.2% | 0.0% |
| Δ8 | 2.2% | 0.0% | 4.1% | 2.3% | 6.4% | 0.0% |
| Δ9 | 12.6% | 10.5% | 11.1% | 9.4% | 9.6% | 11% |
| Δ5 | 5.5% | 8.4% | 5.5% | 3.5% | 3.2% | 8.7% |
| Δ8, 9 | 0.0% | 5.1% | 4.1% | 2.9% | 6.9% | 5.5% |
| Δ5, 8 | 0.0% | 5.9% | 2.3% | 1.8% | 2.7% | 3.2% |
| Δ5, 6 | 7.6% | 3.5% | 3.2% | 1.8% | 3.2% | 4.5% |
| Δ5, 6, 9 | 0.0% | 0.0% | 3.2% | 0.0% | 0.0% | 0.0% |

What is claimed is:

1. An isolated Δ8,9 isoform of IL-23R, said isolated Δ8,9 isoform consisting of SEQ ID NO: 9.

* * * * *